(12) United States Patent
Burleigh et al.

(10) Patent No.: US 7,120,258 B1
(45) Date of Patent: Oct. 10, 2006

(54) APPARATUS AND METHODS FOR MITIGATING IMPAIRMENTS DUE TO CENTRAL AUDITORY NERVOUS SYSTEM BINAURAL PHASE-TIME ASYNCHRONY

(75) Inventors: Joan M. Burleigh, Fort Collins, CO (US); Michael W. Thompson, Waco, TX (US); Susan P. James, Bellvue, CO (US); Michael L. Peterson, Orono, MN (US)

(73) Assignee: Able Planet, Inc., Lakewood, CO (US)

( * ) Notice: Subject to any disclaimer, the term of this patent is extended or adjusted under 35 U.S.C. 154(b) by 825 days.

(21) Appl. No.: 10/110,035

(22) PCT Filed: Oct. 5, 2000

(86) PCT No.: PCT/US00/27460

§ 371 (c)(1),
(2), (4) Date: Apr. 5, 2002

(87) PCT Pub. No.: WO01/26420

PCT Pub. Date: Apr. 12, 2001

Related U.S. Application Data

(60) Provisional application No. 60/157,775, filed on Oct. 5, 1999.

(51) Int. Cl.
*H04R 29/00* (2006.01)
(52) U.S. Cl. .......................... 381/60; 600/559; 73/585
(58) Field of Classification Search ................ 381/60; 600/559; 73/585
See application file for complete search history.

(56) References Cited

U.S. PATENT DOCUMENTS

| | | | |
|---|---|---|---|
| 4,556,069 A | 12/1985 | Dalton et al. | 128/746 |
| 5,434,924 A | 7/1995 | Jampolsky | 381/68.4 |
| 5,680,466 A | 10/1997 | Zelikovitz | 381/68.1 |
| 5,729,658 A | 3/1998 | Hou et al. | 395/2.79 |
| 5,825,894 A | 10/1998 | Shennib | 381/60 |
| 6,167,138 A * | 12/2000 | Shennib | 381/60 |
| 6,895,345 B1 * | 5/2005 | Bye et al. | 702/57 |

FOREIGN PATENT DOCUMENTS

| | | |
|---|---|---|
| EP | 0 915 639 A1 | 5/1999 |
| WO | WO 97/23117 | 6/1997 |
| WO | WO 01/26420 | 4/2001 |

OTHER PUBLICATIONS

"Famous Sonic II Hearing Protectors".
Paul L. Michael and Associates, "Attenuation Summary Westone Style #47 Soft P.V.C., Custom", Westone #47 Molded Earplug with Filter, 1989, 1 page.

(Continued)

*Primary Examiner*—Vivian Chin
*Assistant Examiner*—Justin Michalski
(74) *Attorney, Agent, or Firm*—Lathrop & Gage LC

(57) ABSTRACT

Pathological binaural phase time delay (BPTD) asynchrony is measured at a variety of frequencies and to speech stimuli to develop a BPTD profile for a subject. Then a corrective device (600, 1000) is designed to apply clinical BPTD to compensate for the subject's pathological BPTD. An electronic device (500) is used to measure the subject's ability to comprehend words at a variety of relative time delays between ears to estimate the ideal overall relative time delay. The optimal relative phase shift at a variety of frequencies is also measured. An electronic device (600) may be used to correct the pathological BPTD by delaying sound in different frequency bands differently to the target ear, according to the BPTD profile, or a passive filtered earplug (1000) may be used to correct smaller amounts of BPTD.

8 Claims, 15 Drawing Sheets

OTHER PUBLICATIONS

U.S. Appl. No. 60/157,775, entitled "Apparatus and Methods for Mitigating Impairments Due to Central Auditory Nervous System Binaural Phase-Time Asychrony", filed Oct. 5, 1999, 13 pages.

Simon, et al., "The measurement of the lateralization of narrow bands of noise using an acoustic pointing paradigm: The effect of sound pressure level", J. Accoust. Soc. Am. 95, Mar. 1994, p. 1534-1547.

Willeford, J., "Assessing Central Auditory Behavior In Children: A Test Battery Approach", Central Auditory Disfunction, p. 43-72 (1977).

Noffsinger, D., et al, "Auditory and Vestibular Aberrations in Multiple Sclerosis", The Amqvist and Wiksell Periodical Company, Stockholm, Sweden, p. 1-63 (1972).

Burleigh, J., Thompson, M., James, S., Peterson M., McIntosh K., & Boardman T. (Nov. 2000). *Accommodation of Interaural Timing Differences in Central Auditory Processing Disorders*. Paper presented at the meeting of the American Speech-Language-Hearing Association Convention, Washington, D.C.

Burleigh, J. Time-Rate Expanded Speech and Central Auditory Nervous System Dysfunction, Unpublished Doctoral Dissertation, Colorado State University, 1996.

Gramma, Susan. (Mar. 2002) Focusing on Hyperactivity, *Today's Chemist at Work*, vol. 10, http://pubs.acs.org/subscribe/journals/tcaw/11/i03/html/03health.html.

Burleigh, J., McIntosh, K., and Thompson, M. (2002) Central Auditory Processing Disorders, *Sensory Integration: Theory and Practice* (Eds, Bundy, Lane and Murray) 2$^{nd}$ Edition, F.A. Davis Company, Philadelphia.

Burleigh, J.M., Thompson, M.W., James, S., Peterson, M.L., McIntosh, K.W. & Boardman, T. "Accomodation of Interaural Timing Differences in Central Auditory Processing Disorders"; Paper presented at the meeting of the American Speech-Language Association Convention, Washington, D.C. (62 pages).

Burleigh, J. Time Rate Speech and Central Auditory Nervous System Dysfunction, Unpublished Doctoral Dissertation, Colorado State University, 1996; pp. 1-xiii and 1-162.

Grammer, S. "Focusing on hyperactivity", Today's Chemist at Work, vol. 11, Mar. 2002 http://pubs.acs.org/subscribe/journals/tcaw/11/i03/html/03health.html; pp. 41-42, 45.

Burleigh, J.M., McIntosh, K.W., Thompson, M.S. "Central Auditory Processing Disorders", Sensory Integration: Theory and Practices (2002) (Eds, Bundy, Lane & Murray (2nd Edition), F.A. Davis Company, Philadelphia.

* cited by examiner

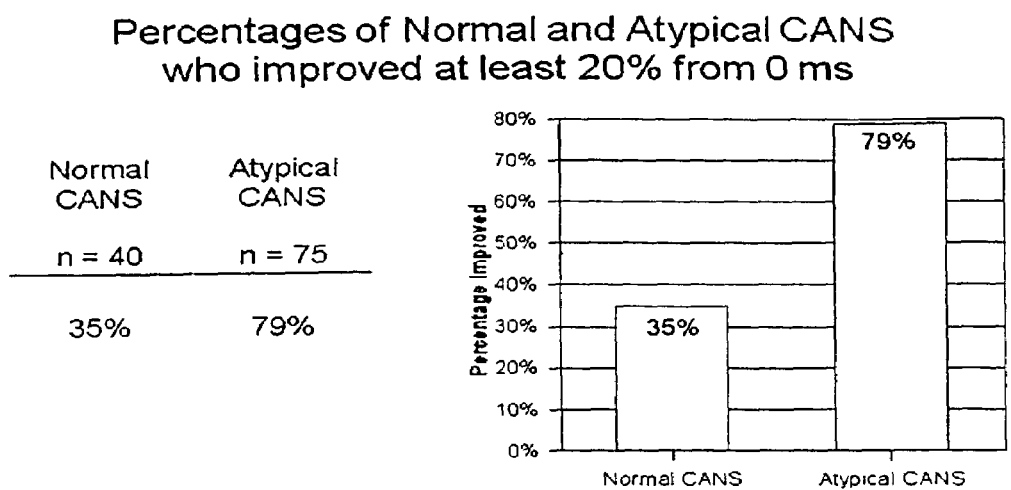
FIGURE 11
FIGURE 14
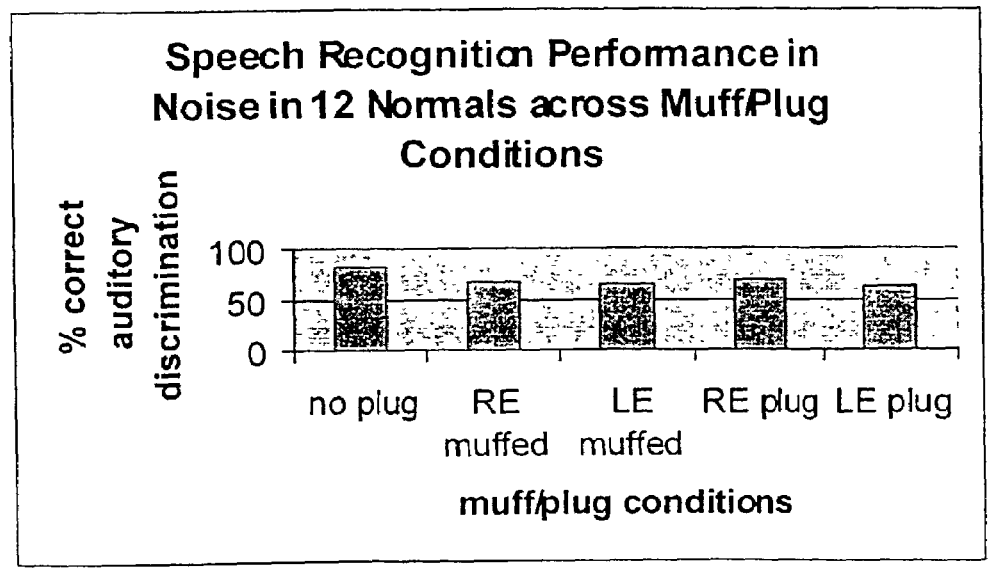

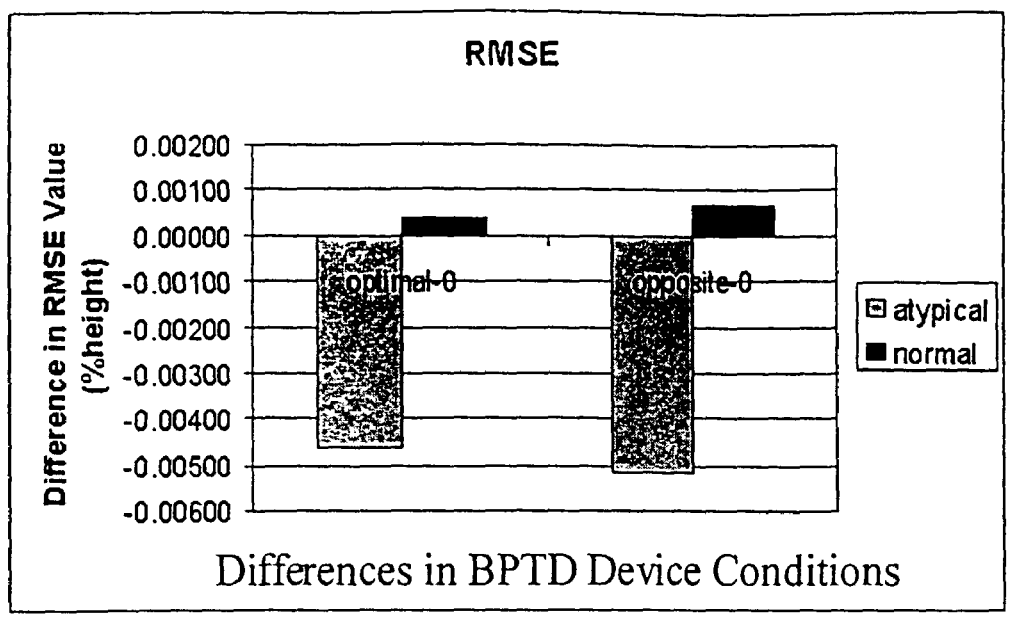
FIGURE 18
FIGURE 19
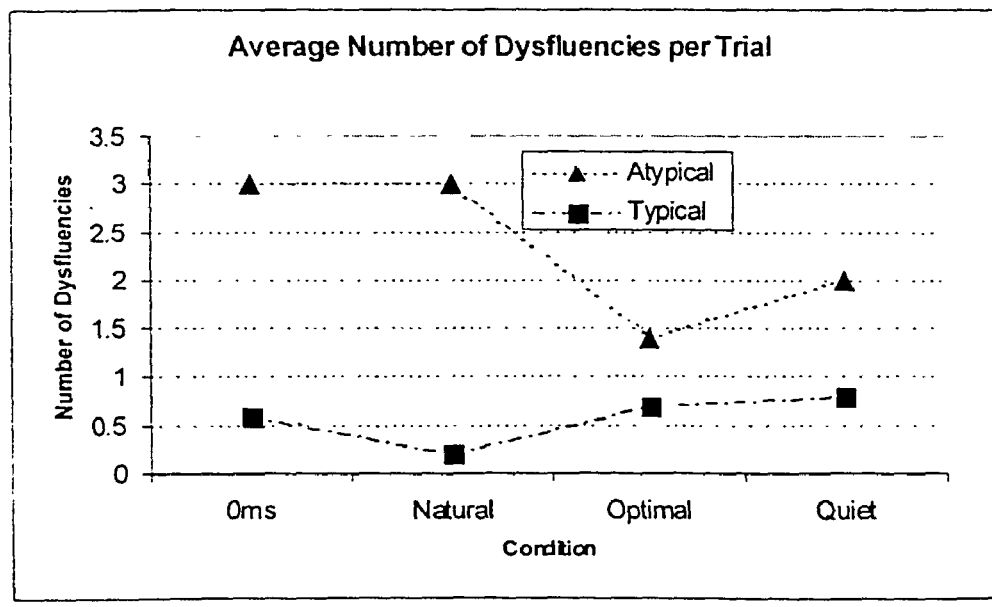

APPARATUS AND METHODS FOR MITIGATING IMPAIRMENTS DUE TO CENTRAL AUDITORY NERVOUS SYSTEM BINAURAL PHASE-TIME ASYNCHRONY

This application is a National Phase Application filing under 35 U.S.C. 371 of International Patent Application, Ser. No. PCT/US00/27460, filed 5 Oct. 2000, which claims the benefit of U.S. Patent Application No. 60/157,775 filed 5 Oct. 1999, each hereby incorporated by reference.

BACKGROUND OF THE INVENTION

1. Field of the Invention

The present invention relates to apparatus and methods for diagnosing, quantifying, and correcting for human central auditory nervous system (CANS) impairment, and in particular binaural phase time delay asynchrony.

2. Description of the Prior Art

Preliminary studies indicate an important connection between the binaural synchronization of the central auditory nervous system (CANS) and gross, fine and oral motor function. A binaural phase time delay (BPTD) is defined herein as a synchronization disruption (delay) in phase and time of the auditory input signals to the two ears. Two types of BPTDs have been defined by the investigators: pathological BPTDs which are "built-in" to a person's CANS, as is the case with a person with neurological injury or disease process, and clinical BPTDs which are induced in a person's CANS using an external device, to compensate for a pathological phase time delay.

A BPTD is a combination of a phase shift and a time delay. For pure tones, a specific phase shift results in a specific time delay. For example, at 1000 Hz a 180° phase shift results in a 0.5 ms time delay. However for speech and other multi-frequency sounds, one specific time delay would result in several different frequency-dependent phase shifts. Note that a time delay can be much larger than the maximum phase shift for a given frequency.

Operationally, binaural interaction of the CANS requires the two ears to integrate dichotic signals separated in time, frequency, and/or intensity. The brain stem is crucial for binaural interaction of acoustic stimuli. Stillman (1980) has emphasized that precise timing of excitatory and inhibitory inputs to each cell along the auditory pathway is critical if each cell is to respond in an appropriate manner. Oertel (1997) has also studied the effects of timing in the cochlear nuclei. The superior olivary complex is an important relay station of the ascending tract of the CANS and is critical for binaural listening capabilities. It is this cross correlation behavior of the two ears that afford the selective listening capability in noisy environments, and the ability to spatially localize sound sources. However, it has been shown that signals from the two ears must have synchronized arrival times for binaural cells to be activated in the superior olivary complex. A delayed signal from one ear negates a binaural response. There is evidence that the synchronization of auditory stimuli is important above the superior olivary complex, at the levels of the brainstem and cerebral cortex.

In individuals (adults and children) with an impaired CANS, a pathological BPTD has been observed between the two ears which is in some cases is quite large (15–20 msec). The pathological BPTD not only decreases speech intelligibility in complex listening environments, but also (somewhat surprisingly) degrades motor (gross, fine, oral) and visual performance. Furthermore, a clinically-induced BPTD, designed to compensate for the pathological BPTD in the subject, significantly improves the speech intelligibility, gross and oral motor function the subject.

It is well known that head injury frequently results in generalized trauma to the brainstem and to higher cortical mechanisms which include the central auditory nervous system, resulting in central auditory processing function abnormalities. Other conditions such as sensory integration problems, speech and language delays, hearing impairment, learning disabilities, multiple sclerosis, Parkinson's Disease, autism, stuttering, developmental delays, central auditory processing disorders, psychological disorders, and neurological disorders have been associated with CANS dysfunction. Individuals with central auditory processing problems often demonstrate difficulty comprehending and remembering auditory information. In addition, these individuals have particular difficulty attending to auditory information in the presence of auditory distractions.

In some traumatic brain injuries and other debilitative neurological brain disorders, the processing of information by the central auditory nervous system is impaired and affects comprehension and recall of auditory information. Operationally, the central auditory nervous system typically receives auditory information from both ears and integrates the input received, even though the acoustic signals received by the ears may be somewhat separated in time, frequency, and/or intensity. Such binaural integration by the central auditory nervous system may be substantially provided in the brain stem. Further, it has been observed that the precise timing of excitory and inhibitory inputs to cells of the central auditory nervous system can affect these cells' behavior to respond appropriately. In particular, it has been shown that auditory signals from both ears must have a relatively synchronized arrival time for certain binaural cells to be activated in the superior olivary complex. Thus, a delayed (e.g. millisecond) response from one ear can impair the integration of binaural response. This is not reflected in the function of the inner ear. However, an individual with a peripheral hearing loss may also have CANS dysfunction or a mechanical effect that creates a disruption of the synchrony between the two ears.

Behavioral and physiological (auditory brainstem response, middle latency response, cortical evoked potentials and mismatched negativity) methods have been employed to measure time parameters of the central auditory nervous system. Previous studies, however, have only analyzed the relationship of timing differences with respect to various pathologies (e.g. a latency in response has occurred). In particular, the development of tests quantifying the changes in auditory input between a subject's ears has been solely used as a diagnostic procedure for identifying a central auditory processing dysfunction. Since the anatomy of the brain stem indicates links between binaural signal processing and integration and motor control, it is not surprising that disorders of the central auditory nervous system often affect other functions such as sensory perception, integration, fine and gross motor, oral motor and visual processing. Accordingly, it would be useful to provide procedures and a diagnostic device that more accurately identify and quantify binaural processing disorders and the relationship of such disorders to other neurologically-based abnormalities. Further, it would also be useful to have a device that subjects manifesting binaural dysfunction-derived disorders can utilize to enhance day-to-day activities so that there may be enhanced speech understanding and recognition, concentration, gross motor movements (e.g. walking), fine motor movements (e.g. writing), oral-motor movement (e.g. speaking) or visual function.

The following references are relevant to the present invention:

U.S. Pat. No. 5,434,924 to Jampolsky; "Two New Methods for Assessment of Central Auditory Function in Cases of Brain Disease," Matzker, Annals Of Otology, Rhinology, & Laryngology 68, 1185–1196, 1959; "Auditory and Vestibular Aberrations in Multiple Sclerosis," Noffsinger et al, Acta Otolaryngologica, 303 (Suppl.), 1–63, 1972; "Assessing Central Auditory Behavior in Children," Willeford, Central Auditory Disfunction, 43–72, 1977; and Westone style # 47 Soft PVC Custom Molded Ear Plug with Quiet Tech Int. Filter.

A need remains in the art for apparatus and methods for diagnosing, quantifying, and correcting for binaural phase-time delay asynchrony.

SUMMARY OF THE INVENTION

It is an object of the present invention to provide apparatus and methods for diagnosing, quantifying, and correcting for binaural phase-time delay asynchrony.

The ideal overall relative time delay portion of the BPTD for the subject is measured by separating the high and low frequencies of a variety of words, and time shifting one of the two components relative to the other. The subject's comprehension of the words will be highest or best at that subject's ideal relative time delay. Time delays can also be measured by inducing a preselected time delay of monosyllabic or bisyllabic words in one ear relative to the other ear in the presence of multitalker babble.

A phase analysis test (PAT) measures the appropriate binaural phase shift at a variety of frequencies by assessing the subject's ability to discriminate pure tones from narrow band noise centered in frequency around the target tone. The BPTD device can be used as a diagnostic tool in this situation. The BPTD device is capable of interfacing with standard audiometers to generate two types of stereo signals. One is the target signal that is comprised of a pure tone presented to both ears with a relative phase difference of q degrees between the target tone channels. The narrowband noise signal is also processed by the BPTD device on a stereo basis to generate a relative phase difference of f degrees between the two narrowband noise channels. The BPTD device then mixes these two types of signals together by performing a weighted summation operation and the output can then be presented to the subject. The weighting value on the summation processes is used to vary the signal-to-noise power ratio between the target signal and the noise. Since the resulting output signal is a combination of these two signal types we call it the $S_q N_f$ output signal. The BPTD device can implement a variety of combinations of q and f parameters for research, diagnostic, and accommodative purposes. The PAT test is produced by generating $S_q N_q$ (q=f) output signals over a range of tone frequency and phase (q) values. For each frequency and phase combination the amplitude of the target tone is varied in a procedure to establish the minimum target strength level needed to hear the target signal in the presence of narrowband noise. For diagnostic purposes, threshold results from a specific $S_q N_q$ at various frequencies represent the baseline condition. Normative threshold measures for each target frequency and phase value tested will be used to determine atypical phase results for various frequencies.

The optimal phase value for a given operating frequency for accommodative purposes is the one in which the tone is heard at the lowest hearing threshold value. An operator interface allows the BPTD device to be used to systematically collect the optimal phase values over the range of test frequencies.

The PAT test also includes the synthesis of all of the phase information to form a phase correction filter as illustrated in FIG. 9. The BPTD device also has the capability of implementing the phase correction filter in real-time. With the correction filter in place, a speech stimulus can be used to repeat the phase analysis paradigm described above. However, since speech is a frequency rich stimulus, the narrow-band noise is replaced with noise that has a broader frequency profile, such as broad-band or white noise. As before, a procedure for determining the minimum hearing threshold for when the target speech signal is heard above the broad-band noise signal is implemented. Comparisons can then be made to the situation where the correction filter is not in place and performance improvements can be verified. It should also be noted that the phase correction filter can be compared or combined with optimal time delay parameters (such as those obtained from the Delayed Binaural Fusion Test). Furthermore, the BPTD device is capable of implementing this hearing threshold approach to investigate and diagnose time delay parameters such as those considered for the Delayed Binaural Fusion Test.

An electronic device is used for diagnosing and measuring the phase and time portion of BPTD, and verifying the best overall relative time delay for the subject. An operator controls the relative time delay and phase delay applied to the subject's ears via an operator interface. The test set up considers one frequency (tone) at a time and applies the selected phase shift (and/or time delay) to whatever frequency is applied. The operator interface may include a keypad to enter control signals, and a display to show which control signal is being applied. Control signals set the amount of phase shift to be applied. The relative time delay shifter applies the overall relative time delay, and the phase shifter applies the phase shift.

A real time, active, digital signal processing electronic device is used for correcting BPTD, once it has been measured in the testing phase. Equivalent analog devices could also be used, but digital devices are more practical. In general, only one of the devices will be used, since sound is typically delayed to the same ear at every frequency.

Sound enters a microphone, which turns it into an analog electrical signal representing the sound. The signal is amplified by a preamp, and is digitized in an analog to digital converter (ADC). A digital signal processor (DSP) operates much as the test device operated, applying an overall relative time delay and a phase shift profile. A digital to analog converter (DAC) converts the processed signal back to an analog signal, an amplifier filters and amplifies the signal, and a microphone turns the signal into an audio signal to be delivered to the ear of the subject.

The BPTD applied by the DSP is programmed according to the overall relative time shift and the phase shift versus frequency profile obtained in the testing phase. The BPTD profile is unique for each subject. The DSP could be reprogrammable, via a control signal, so it could be optimized for the wearer in actual use. Note that other hearing aid processing (compression or the like) may also be incorporated into the DSP if desired. Amplitude changes may also be implemented. In addition, the BPTD profile used may change with the kind of background noise detected by the device, or the type of activity the subject is performing.

A physical filter (a passive earplug) may alternatively be used for correcting BPTD. A physical device in the ear can delay the sound in the ear, and can delay different frequencies differently, as an electronic device does. The passive earplug induces a BPTD to sound entering the ear by altering the propagation time of the acoustic waves. The primary method of delaying an acoustic signal in this manner is through the use of ducting, through which the signal propagates. The velocity of propagation of sound in air is approximately 331 meters per second, and the length of the ducting in the ear canal is about 10 cm (ducting along an eyeglass frame can be longer). Thus the time delay applied by a passive device in the ear canal is on the order of 30 us, corresponding to a phase shift of about p/3 at 5000 Hz. This time delay may be increased by about a factor of two by using a fluid rather than air in the ducting. In addition to the overall delay created by ducting, the frequency response of the earplug may also be tuned by using acoustical filter elements. Standard elements include chambers, Helmholtz resonators, and dampers. In addition, other acoustic elements such as horns, collectors, domes, trumpets, and resonators may be used.

BRIEF DESCRIPTION OF THE DRAWINGS

FIGS. 11–19 are charts illustrating test results for an embodiment of the present invention.

DETAILED DESCRIPTION OF THE PREFERRED EMBODIMENT

Figure 1:
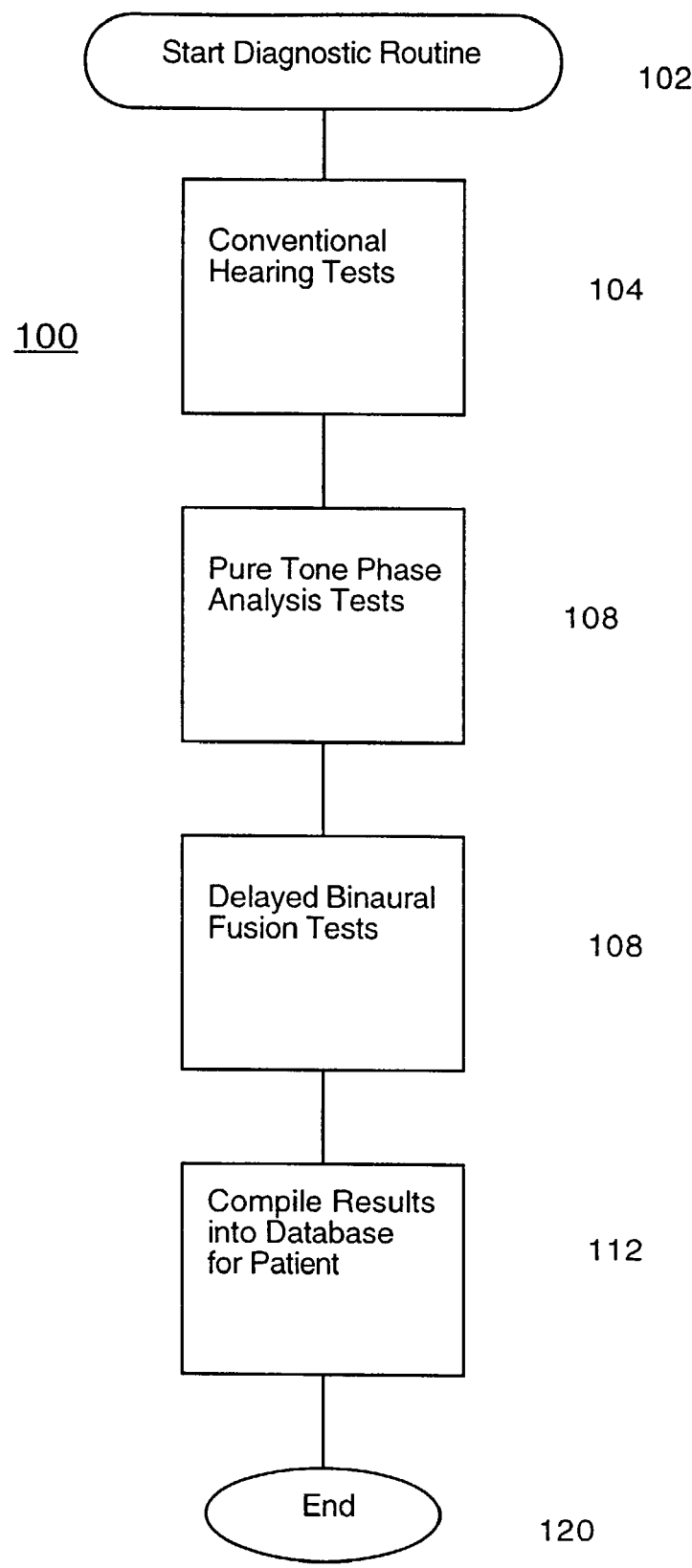
FIG. 1 is a flow diagram showing a set of diagnostic procedures for diagnosing and quantifying pathological binaural phase time delay (BPTD) in subjects.

FIG. 1 is a flow diagram 100 showing a set of diagnostic procedures for diagnosing and quantifying pathological binaural phase time delay (BPTD) in subjects. The tests may be performed in any order, but the order shown is the most logical, for reasons described below.

The test routine begins with step 102. In general it will be desirable to perform a series of conventional hearing tests 104 on the subject first, in order to determine whether other hearing problems or central auditory processing problems exist. These tests are shown in more detail in FIG. 2. Next, a series of pure tone phase analysis tests 108 are performed to determine the optimal clinical phase shift at a variety of sound frequencies. The subject's ability to identify a tone out of noise centered around the tone and the resultant threshold is assessed at a variety of relative phase shifts between ears, and at a variety of frequencies, and a profile of the subject's phase shift frequency profile is generated. The frequency profile will be used to complement a phase correction filter. With this filter in place, speech stimuli can be used as a target in a similar fashion with broad band noise. These tests are shown in more detail in FIG. 3.

Finally, a series of delayed binaural fusion tests are performed. These tests assess comprehension of words at a variety of relative time delays between ears, and at a variety of frequencies. Again the results of this test are used to develop the subject's time delay versus frequency profile. This test is matched up to the pure phase test to complete the BPTD profile. This test also allows for testing of relative shifts greater than one wavelength, which cannot be done with tones. FIG. 5 shows an embodiment of an electronic device that assists in performing the tests of FIGS. 3 and 4.

In step 112, the results for the subject are compiled in a database. If the pathological BPTD for the subject is significant, this database is used to design an electronic filter (see FIG. 6) or a physical filter (see FIG. 7) to apply compensating clinical BPTD to the subjects ears.

Figure 2:
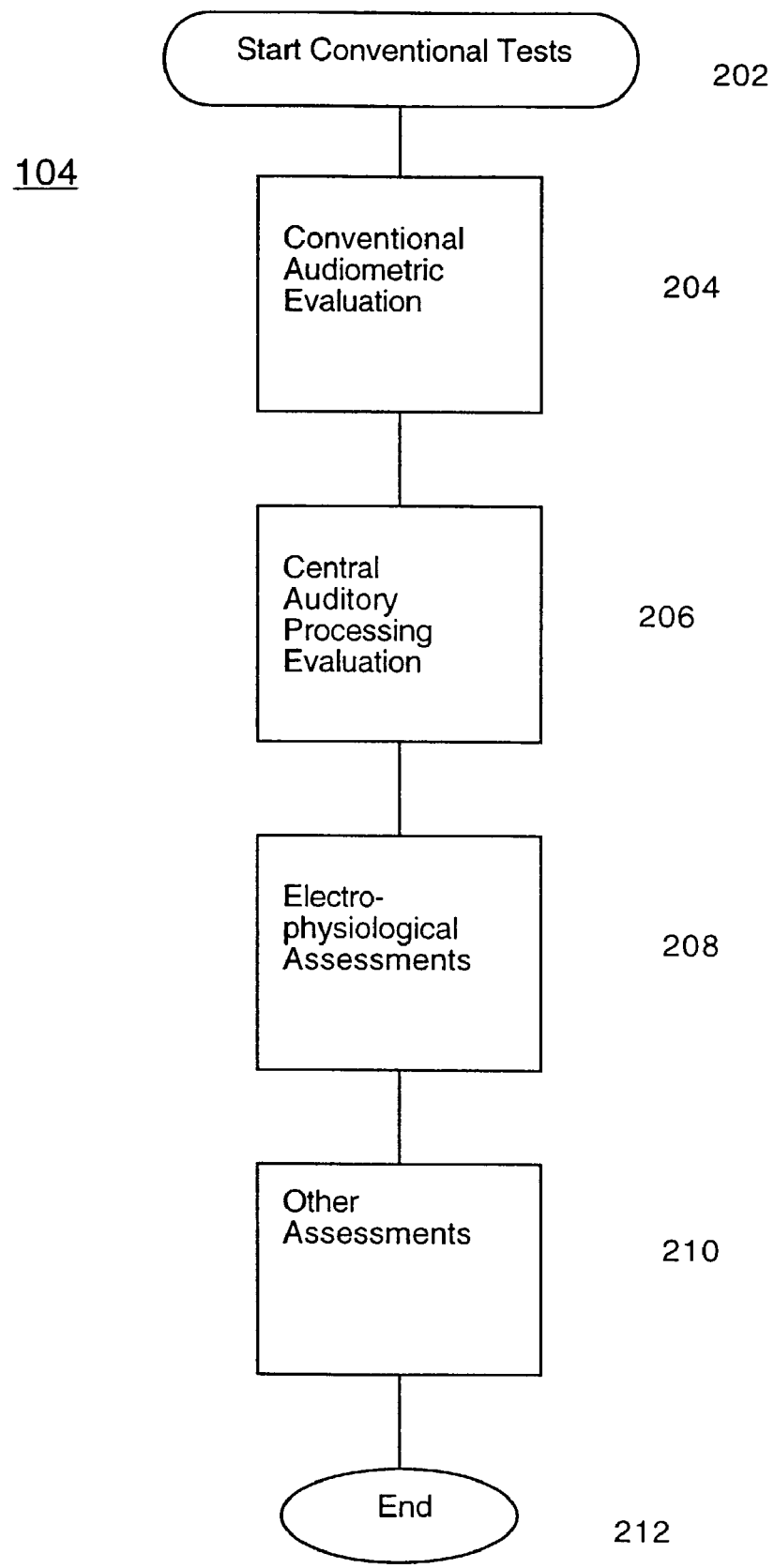
FIG. 2 is a flow diagram showing the conventional tests performed in FIG. 1, in more detail.

FIG. 2 is a flow diagram showing conventional tests 104 in more detail. The conventional tests start at step 202. In general these tests include a pure tone evaluation 204 to evaluate hearing loss at various frequencies. A central auditory processing evaluation 206 is performed, and various electro-physiological assessments 208 are performed. Other assessments 210 may be added. The conventional tests end at step 212.

Central auditory processing evaluation 206 may include (but is not limited to) such tests as: Willeford central auditory test battery; Dichotic digits test; Ipsilateral/contralateral competing messages; Synthetic sentence identification with contralateral competing messages; Masking level differences; Auditory duration patterns; Speech-innoise; Pediatric speech intelligibility test; segment altered CVCs; pitch patterns; dichotic chords; compressed speech, with and without reverberation.

Electro-physiological assessments include such tests as: ABR; Middle latencies; Late latencies; P300; Mismatched Negativity. Binaural interaction components will also be calculated. Since electrophysiological measurements use various latency classifications or markers, this information may yield added information to the diagnosis and quantification of auditory asynchronies.

Figure 3:
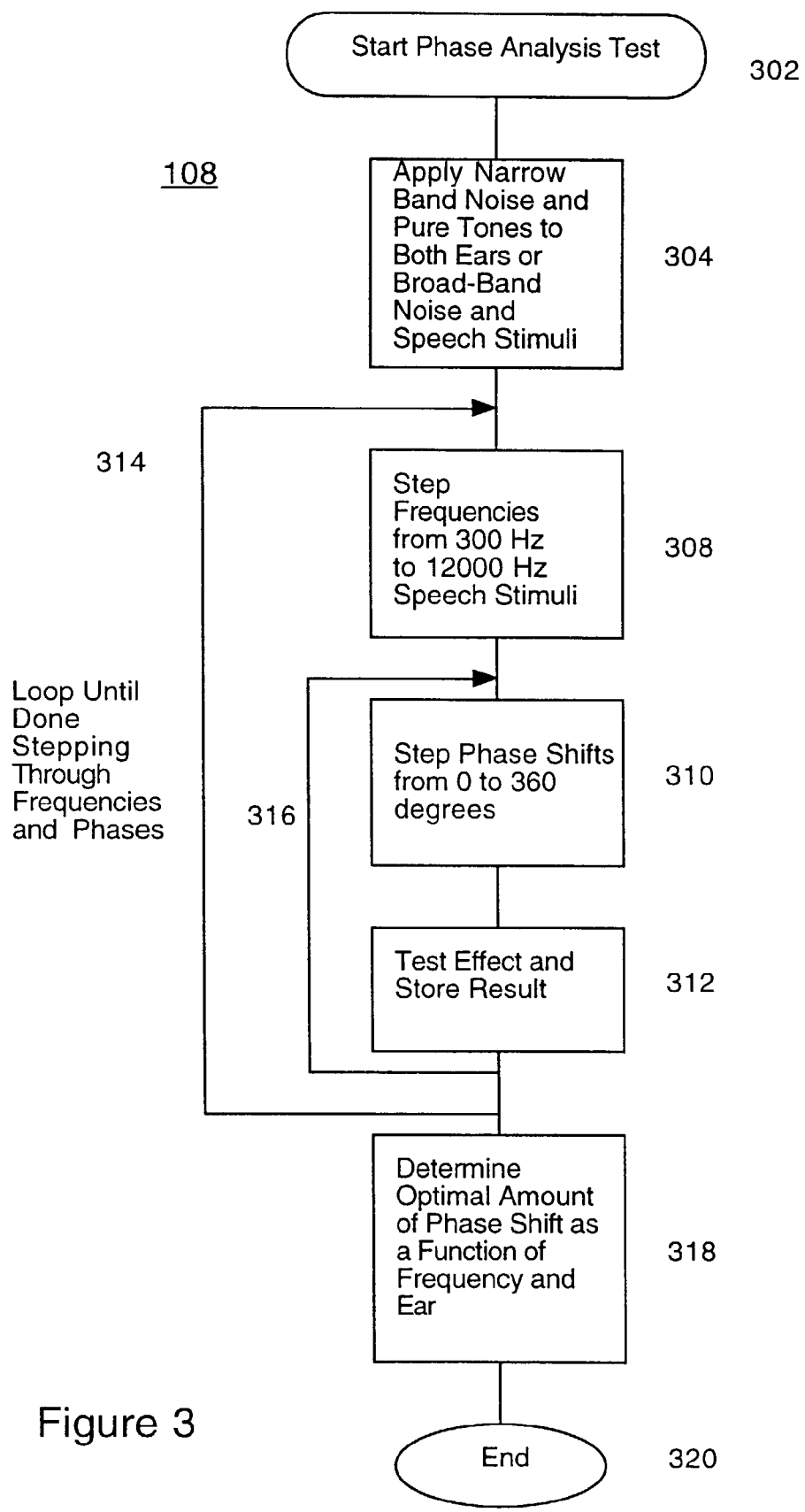
FIG. 3 is a flow diagram showing the phase analysis tests performed in FIG. 1, in more detail.

FIG. 3 is a flow diagram showing the pure tone phase analysis test 108, according to the present invention. A device such as that shown in FIG. 5 may be used in this test. This test assesses the subject's ability to discriminate pure tones from narrow band noise centered around the tone. The pure tone and the noise are presented to each ear at a different phase (giving a relative phase shift or clinical BPTD). Thresholds are obtained for each tone at varying phase shifts. In the preferred embodiment, a relative phase shift is selected, and the amplitude of the tone is increased until the subject can pick it out of the noise. The optimal phase shift is the phase shift that produces the smallest amplitude hearing threshold.

The test starts at step 302. Narrow band noise and pure tones are applied to both ears in step 304. In outer loop 310, frequencies are stepped through, for example from 500 Hz to 12000 Hz. In inner loop 311 phase shifts of the pure tone between the two ears are stepped through for each frequency, for example 30, 60, 90, 120, and 180 degrees. These two loops can be exchanged if desired.

Step 312 tests the subject's threshold for the pure tone at that frequency and phase shift, and stores the result, for example in a table. Step 314 determines the optimal relative phase shift between ears at each tested frequency, by determining at which phase shift the tone was heard best (at the lowest amplitude) over the background noise, for each frequency, compared to normal phase shift function. Thus a clinical phase shift versus frequency profile has been developed to compensate for the phase portion of the subject's pathological BPTD. The phase analysis test ends at step 320. This test procedure is also used with speech stimuli as the target signal using a phase correction filter and broad band noise.

Figure 4:
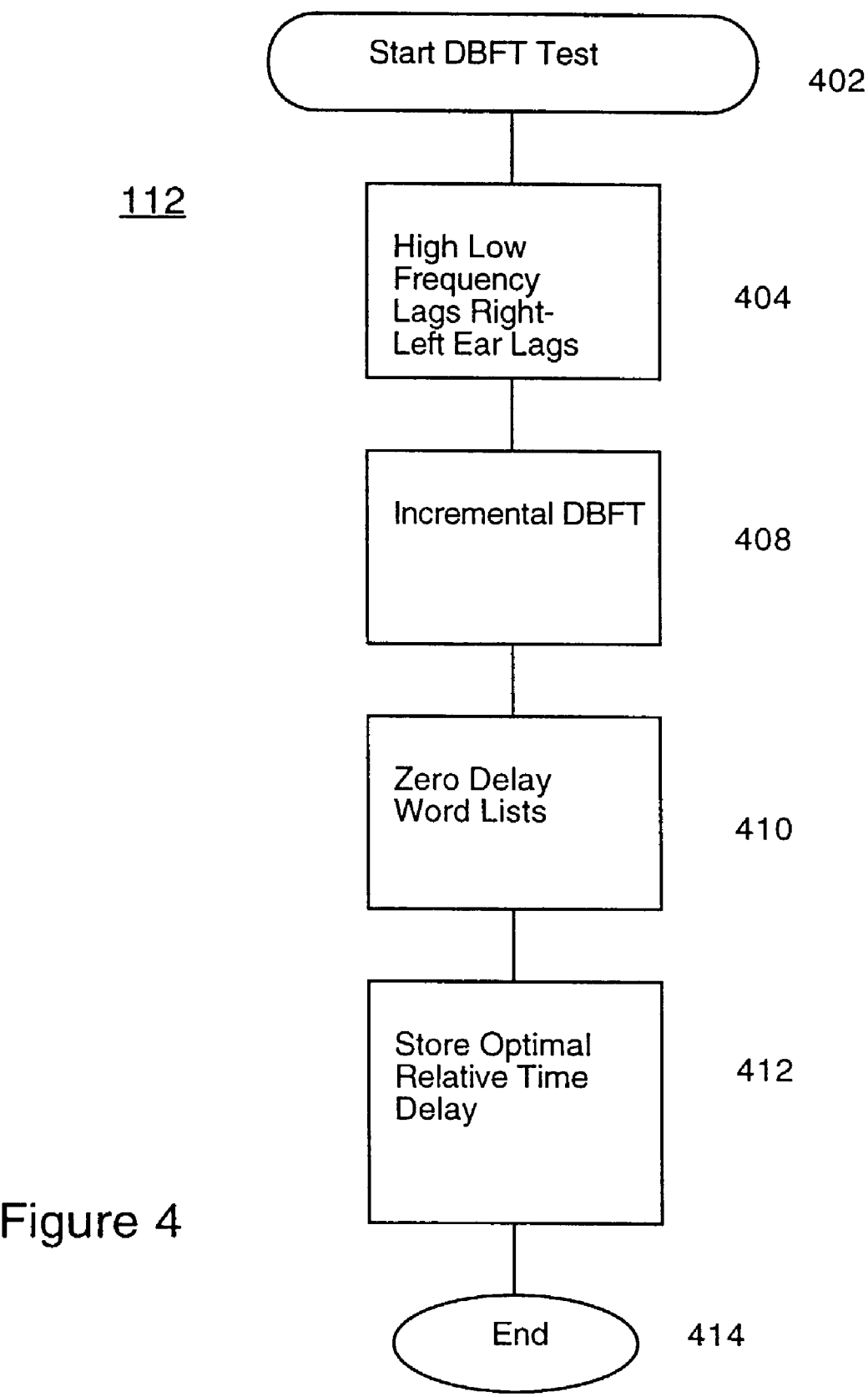
FIG. 4 is a flow diagram showing the delayed binaural fusion tests performed in FIG. 1, in more detail.
Figure 5:
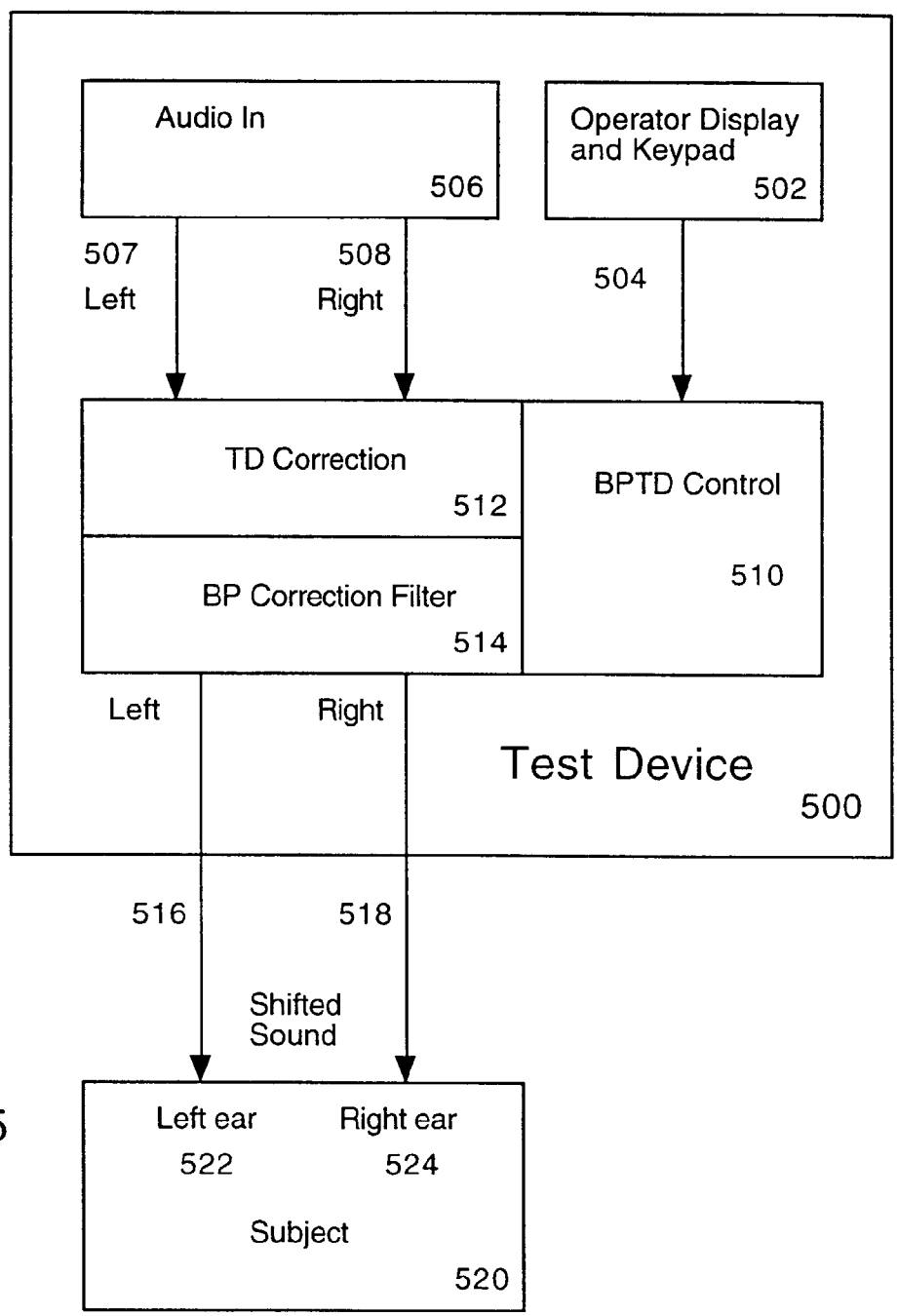
FIG. 5 is a block diagram of an electronic device for diagnosing and measuring BPTD.

FIG. 4 is a flow diagram showing delayed binaural fusion test 112. This test measures the subject's ability to comprehend words (preferably bisyllabic) at various time delays between the two ears. Thus, it provides information regarding timing differences between the two ears and adds information beyond the phase analysis test. Examples of the tests done are given below.

The test starts at step 402. High Low Frequency Lags Test 404 tests comprehension of a series of bisyllabic words separated into two frequency components (e.g. a high frequency component from 1900–2100 Hz and a low frequency component from 500–770 Hz) presented at a variety of relative time delays to the ears. The purpose of step 404 is to determine whether a significant impairment due to CANS binaural phase-time asynchrony exists for the subject. For a person without this type of impairment, the change in relative time delays does not significantly effect comprehension—the CANS can account for the changes. In addition, the best comprehension occurs for the case of no relative time delay, as would be expected. For a person with significant impairment due to CANS binaural phase-time asynchrony, however, different relative time delays result in very different levels of comprehension, and the best comprehension occurs at a relative time delay other than zero. If the results of step 404 indicate that a CANS-BPTD impairment exists, step 408 determines the optimal time delay for the subject.

Each word is presented to both ears, the high frequency portion of the word going to one ear and the low frequency portion of the word going to the other ear. The relative time delay between the ears is changed for each word, and a variety of words are used at each relative time delay. The words are generally bisyllabic, familiar to most people, and the emphasis is placed on both syllables equally (e.g. woodwork, bedroom, inkwell). For example, a series of 120 words may be used, divided among the selected relative time delays. Other speech stimuli can be used along with other novel ways to split or partition out speech segments. A computer program for sequentially selecting the words and setting the relative time delay for each word makes this process much easier. The program may also provide a score sheet for entering whether each word was correctly identified, and computing the correct averages at each phase shift.

Steps 404 and 408 zero in on the ideal clinical relative time delay, because it is difficult for a subject with CANS-BPTD impairment to understand a word if the high and low frequency components are not correctly time shifted relative to each other, or when they are lagged while being embedded in noise or speech-babble. In other words, auditory discrimination improves with an induced time delay in one ear for individuals with a CANS disfunction. Other speech modifications using a lag paradigm may be used for identifying and quantifying asynchronies.

The described tests are scored by computing the percentage of correct responses given by the subject at each relative time delay, and each step refines the results of the previous step. A software program for sequentially selecting the words and setting the relative phase shift for each word makes this process much easier. The program also provides a score sheet display for entering whether each word was correctly identified, and computes the correct averages at each phase shift when the test is completed. The phase shifts tested may be selected in view of the ideal overall clinical phase shift that was computed at the end of the pure tone or speech phase test of FIG. 3, in order to make this test more efficient.

High-low frequency lags test 404 tests comprehension of a series of words at (for example) relative time delays of 5, 10, 15, and 20 msec to the left and right ears. The best comprehension level might be achieved at, for example, 5 msec time delay to the right ear. Incremental DBFT test 408 then tests comprehension of a series of words at relative time delays of 2.5, 5, and 7.5 msec (assuming a 5 msec delay gave the best results in step 404). The best comprehension level might be achieved at, for example, 7.5 msec time delay. Those skilled in the art will appreciate that further fine tuning can be accomplished with smaller relative time delays using the BPTD diagnostic device, if desired.

Zero delay word lists test 410 then verifies the results from steps 404 and 408 by testing comprehension at the selected relative time delay, using a device such as that shown in FIG. 5.

Step 412 stores the optimal time delay selected by the previous steps. The test ends at 414. A correction device such as that shown in FIG. 6 may now be designed, by combining the results of the Phase Analysis Test shown in FIG. 3 and the DBFT test shown in FIG. 4.

FIG. 5 is a block diagram of an electronic device 500 for diagnosing and measuring the phase and time portions of BPTD, and for verifying the best overall relative time delay for the subject (see FIG. 4, step 408). An operator controls the relative time delay and phase delay applied to the subject's ears via an operator interface 502. The test setup shown in this figure tests one frequency (tone) at a time and applies the selected phase shift to whatever frequency is applied. The steps of the phase shift test are shown in FIG. 3.

Operator interface 502 may include, e.g. a keypad to enter control signals, and a display to show which control signal is being applied. Control signals 504 set the amount of relative time delay and phase shift to be applied by digital signal processor 510. Sound 506 is digitized via channels 507 and 508 (or only one microphone may be used). Relative time delay shifter 512 applies the overall relative time delay per control signals 504, and phase shifter 514 applies the phase shift. The output of block 510 is delivered to the left ear 522 of the subject 520 via signal 516, to the right ear 524 of the subject via signal 518.

Figure 6:
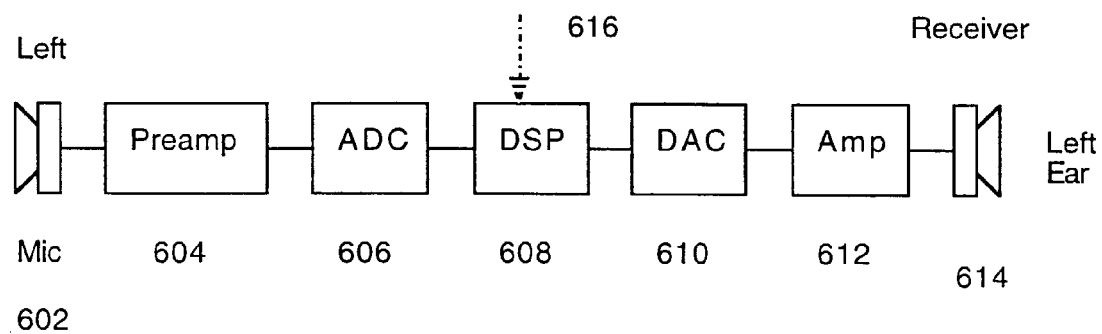
FIG. 6 is a block diagram of an electronic device for correcting BPTD.

FIG. 6 is a block diagram of real time, active, digital signal processing electronic device 600 for correcting BPTD, once it has been measured. Equivalent analog devices could also be used, but digital devices are more practical.

Sound enters microphone 602, which turns it into an analog electrical signal representing the sound. The signal is amplified in preamp 604, and is digitized in analog to digital converter (ADC) 606. Digital signal processor (DSP) 608 operates much as test device 500 in FIG. 5 operated, applying a time delay and a phase shift profile (see FIG. 7). Digital to analog converter (DAC) 610 converts the processed signal back to an analog signal, amplifier 612 filters and amplifies the signal, and microphone 614 turns the signal into an audio signal to be delivered to the ear of the subject.

The BPTD applied by DSP 608 is programmed according to the BPTD versus frequency profile obtained in the testing phase. It is unique for every subject. As an option, the DSP could be reprogrammable, via control signal 616, so it could be optimized for the wearer in actual use. Note that other hearing aid processing (compression or the like) may also be incorporated into the DSP if desired.

Furthermore, we have observed that BPTD's produce a very noticeable auditory effect in the presence of noise regardless of whether the subject has CAP difficulties or not. The fact that the implementation of BPTD parameter changes produce differences in target signal (speech stimuli) perceived loudness in the presence of masking noise indicates that BPTD's have the potential for enhancing hearing aid performance In addition, the BPTD profile used may change with the kind of background noise detected by the device. A different BPTD profile may be used when the wearer is in a noisy environment, for example, or for different actions, as when the wearer is walking rather than sitting and writing.

Figure 7:
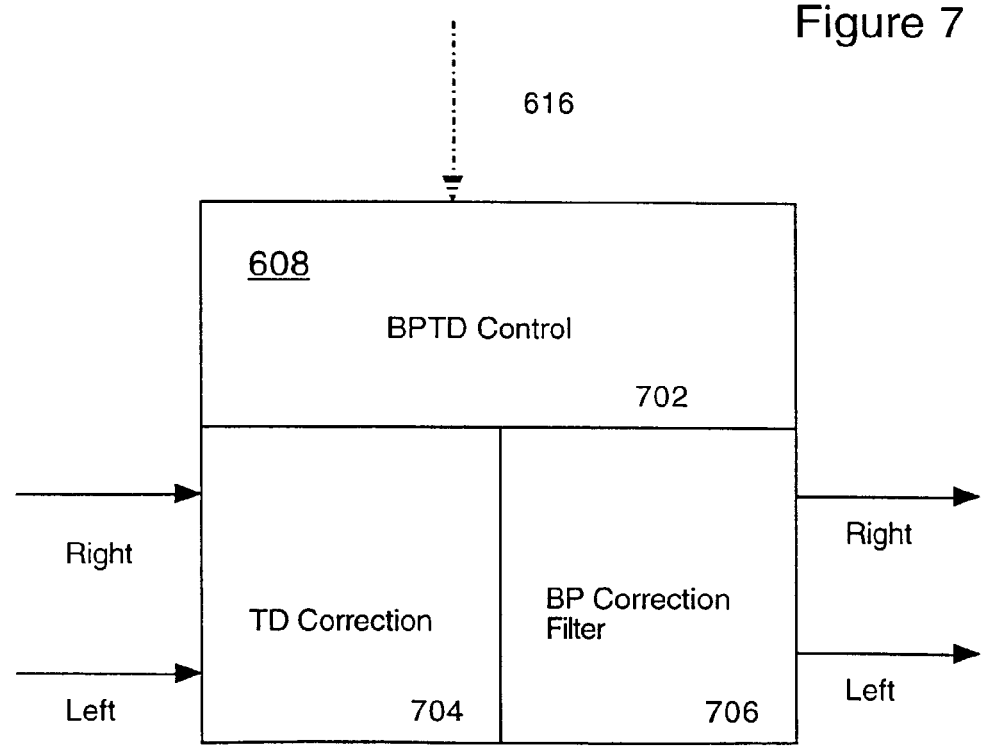
FIG. 7 is a more detailed block diagram of the digital signal processor (DSP) of FIG. 6.

FIG. 7 is a more detailed block diagram of DSP 608 of FIG. 6. BPTD control block 702 (via control signal 616, if used) controls the overall time delay and the phase shift profile applied to the sound signal. TD correction block 704 applies the overall time delay. BP correction block 706 applies a phase shift profile to the sound signal. See FIG. 9 for an example of a phase shift profile.

Figure 8:
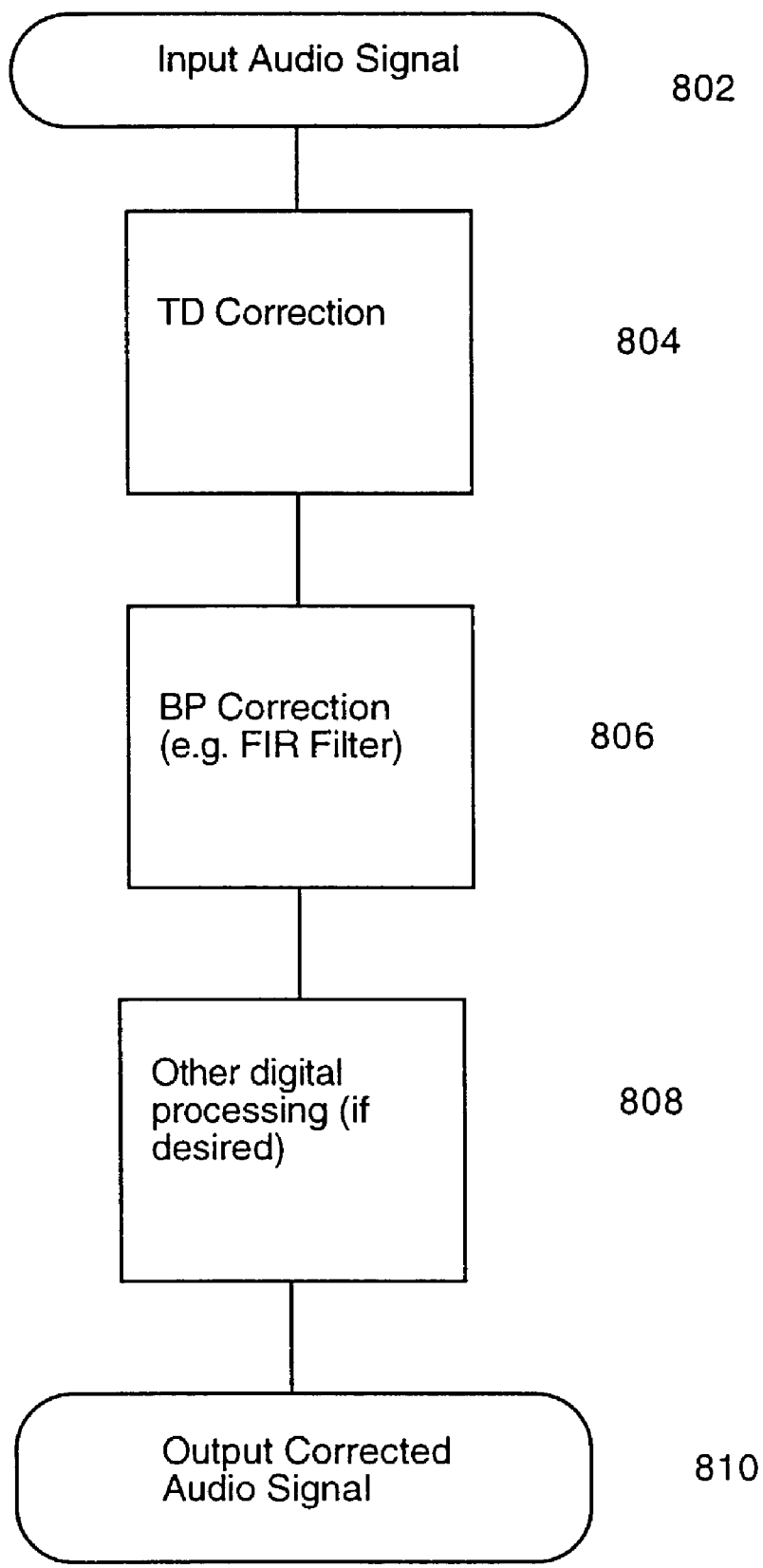
FIG. 8 is a flow diagram showing the process accomplished by the DSP of FIG. 6.

FIG. 8 is a flow diagram showing the process accomplished by the DSP of FIG. 6. The audio input signal is applied in step 802. In step 804, the overall time delay is applied. In step 806, the phase profile is applied. In step 808 other processing is accomplished, if desired (compression or the like). The corrected output signal is output in step 810.

Figure 9:
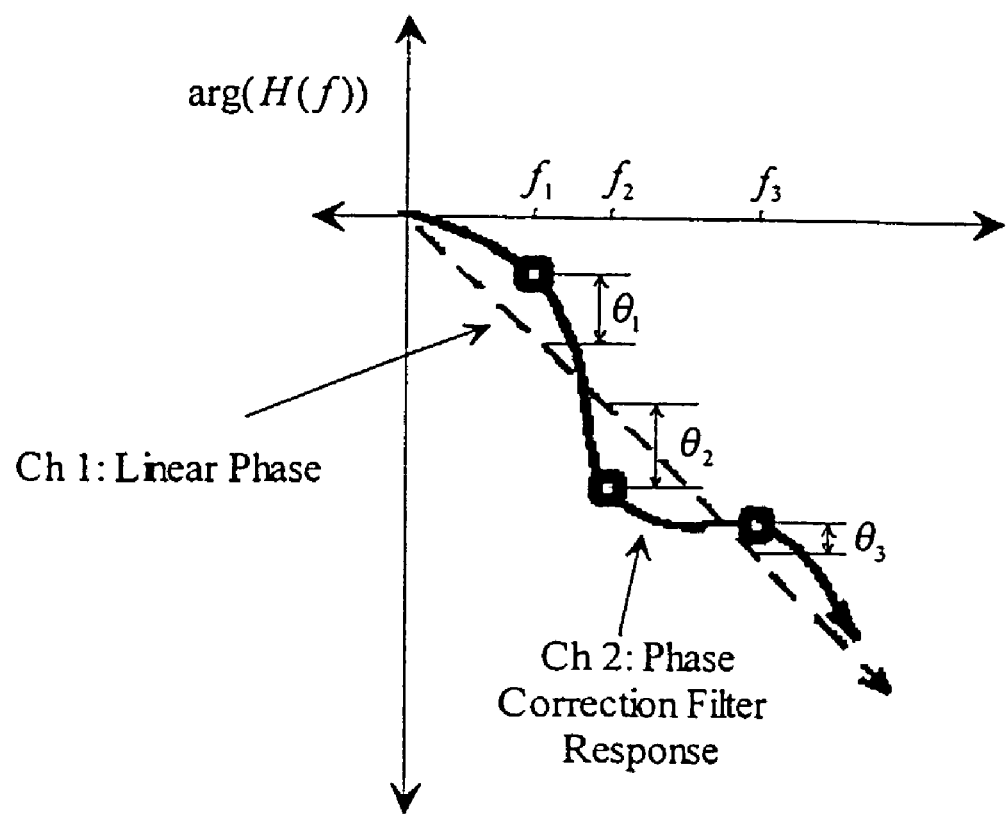
FIG. 9 is a diagram showing an example of the correction accomplished in the BP block of the DSP of FIG. 7.

FIG. 9 is a diagram showing an example of the phase shift profile correction accomplished in BP block 706 of DSP 608 of FIG. 7. Dotted line 902 indicates linear phase, and solid line 904 indicates the phase profile after the phase corrections. $q_1$, $q_2$, and $q_3$ indicate phase shifts at specific frequencies f1, f2, and f3 respectively. Note that a different phase shift is applied at each frequency, and that positive and negative phase shifts may be applied. Of course, the overall time delay applied by block 704 means that, overall, the time delay plus the phase shift will be positive.

Figure 10:
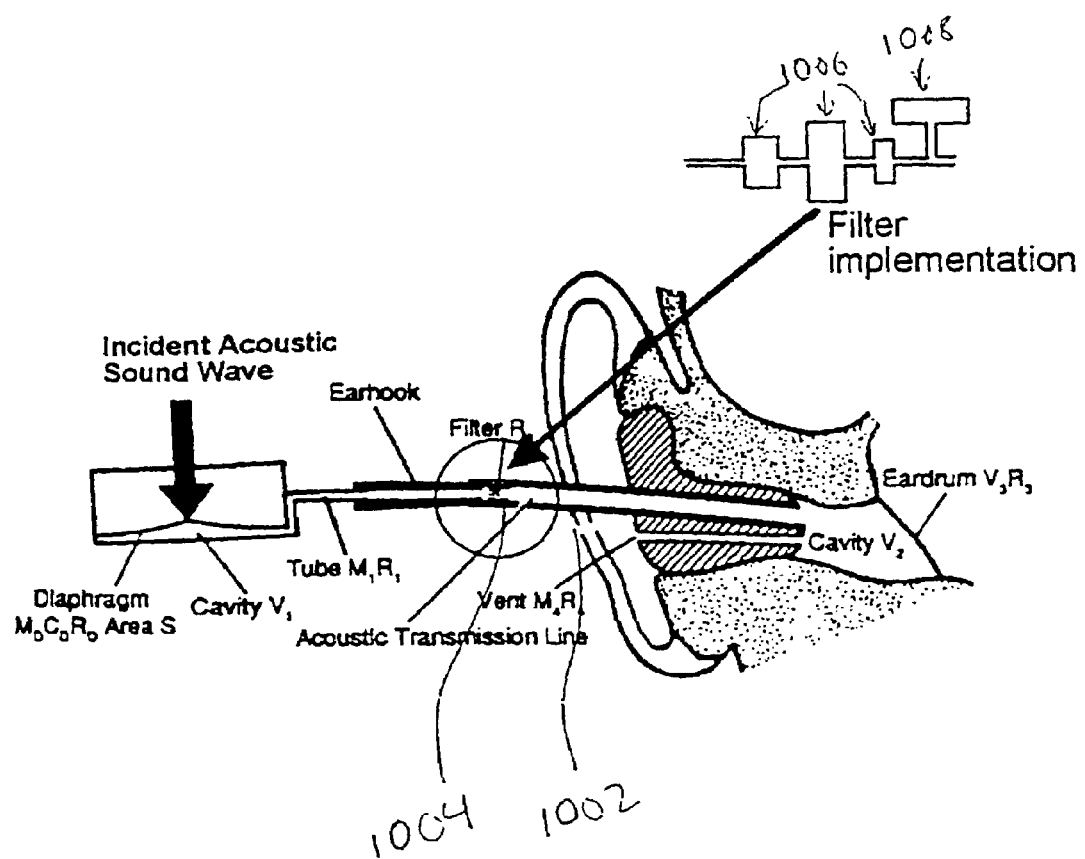
FIG. 10 is a cutaway side view of a physical filter for correcting BPTD.

FIG. 10 is a cutaway side view of a physical filter (a passive earplug) for correcting BPTD. A physical device in the ear can delay the sound in the ear, and can delay different frequencies differently, as electronic device 600 (in FIG. 6) does. However, a physical device is capable of much smaller time shifts, and the control at different frequencies is far less precise. Since the physical device is much cheaper and does not require batteries, it is the preferred device is some cases, for example when a small phase shift or delay is required, and the phase shift required doesn't vary much at various frequencies. The physical filter is also smaller and more convenient.

Passive earplug 1000 induces a BPTD to sound entering the ear by altering the propagation time of the acoustic waves. The primary method of delaying an acoustic signal in this manner is through the use of ducting 1002, through which the signal propagates. The velocity of propagation of sound in air is approximately 331 meters per second, and the length of the ducting in the ear canal is about 10 cm (ducting along an eyeglass frame can be longer). Thus the time delay applied by a passive device in the ear canal is on the order of 30 us, corresponding to a phase shift of about p/3 at 5000 Hz. This time delay may be increased by about a factor of two by using a fluid rather than air in ducting 1002. For example, the velocity of sound in iodine is around 108 m/s.

In addition to the overall delay created by ducting 1002, the frequency response of earplug 1000 may also be tuned to some degree by using acoustical filter elements 1004 (limited by space available). Standard elements include chambers, Helmholtz resonators, and dampers. In addition, other acoustic elements such as horns, collectors, domes, trumpets, and resonator may be used.

A direct analog may be made to an electrical BPTD system such as that shown in FIG. 6, with Helmholtz resonators and expansion chambers used to create filter characteristics. The number of cavities relates to the order of filter that can be designed.

In general, the phase time delay provided by passive element 1000 is dependent on the length of the auditory ducting 1002 within the plug, the diameters and locations of the cavities (side branch chambers 1008 or expansion chambers 1006) and the working fluid in the ducting.

While the exemplary preferred embodiments of the present invention are described herein with particularity, those skilled in the art will appreciate various changes, additions, and applications other than those specifically mentioned, which are within the spirit of this invention.

Appendix A

Examples of Testing Procedures

TABLE 1

Delayed Binaural Fusion Test Table of Words

| List 1 | List 2 | List 3 | List 4 | List 5 | List 6 |
| --- | --- | --- | --- | --- | --- |
| woodwork | redbird | doorbell | sunset | highway | dishcloth |
| chalkboard | desktop | racetrack | bookmark | doormat | handbell |
| shortcake | playground | treetop | meatball | grandson | padlock |
| baseball | icecream | wildcat | headlight | toothbrush | northwest |
| scarecrow | lighthouse | downtown | shipwreck | hardware | hardhat |
| hatrack | armchair | whitewash | bullfrog | flagpole | mushroom |
| housework | corncob | windmill | handshake | hairbrush | eardrop |
| railroad | highchair | tshirt | pancake | airplane | football |
| duckpond | schoolbell | bedspread | bedroom | inkwell | drugstore |
| nightfall | workshop | bluejay | iceberg | keyhole | toolbox |
| stairway | drawbridge | daybreak | birdnest | hottub | teabag |
| beanbag | goldfish | driftwood | dirtbike | mousetrap | lightbulb |
| horseshoe | lefthand | sidewalk | farewell | birdhouse | sandbox |
| farmhouse | shirttail | billboard | bathtub | pinwheel | cowboy |
| starfish | snowball | greyhound | toothpick | earthworm | yardstick |
| doghouse | eyebrow | oatmeal | daylight | iceskate | eardrum |
| cookbook | birthday | snowman | schoolboy | bustop | rainbow |
| offshore | blackboard | stringbean | shoelace | thumbtack | treehouse |
| swingset | shortcut | forehead | dollhouse | hothouse | carwash |
| hotdog | timeout | cardboard | lifeboat | jailhouse | footstool |

TABLE 2

Delayed Binaural Fusion Test Time Delay Sequencing Table

| Condition | List 1 | List 2 | List 3 | List 4 | List 5 | List 6 | Lagging Channel |
| --- | --- | --- | --- | --- | --- | --- | --- |
| 1 | 0 | 5 | 10 | 15 | 20 | 25 | Low Freq. |
| 2 | 25 | 0 | 5 | 10 | 15 | 20 | Low Freq. |
| 3 | 20 | 25 | 0 | 5 | 10 | 15 | Low Freq. |

TABLE 2-continued

Delayed Binaural Fusion Test Time Delay Sequencing Table

| Condition | List 1 | List 2 | List 3 | List 4 | List 5 | List 6 | Lagging Channel |
|---|---|---|---|---|---|---|---|
| 4 | 15 | 20 | 25 | 0 | 5 | 10 | Low Freq. |
| 5 | 10 | 15 | 20 | 25 | 0 | 5 | Low Freq. |
| 6 | 5 | 10 | 15 | 20 | 25 | 0 | Low Freq. |
| 7 | 0 | 5 | 10 | 15 | 20 | 25 | Low Freq. |
| 8 | 25 | 0 | 5 | 10 | 15 | 20 | Low Freq. |
| 9 | 20 | 25 | 0 | 5 | 10 | 15 | Low Freq. |
| 10 | 15 | 20 | 25 | 0 | 5 | 10 | Low Freq. |
| 11 | 10 | 15 | 20 | 25 | 0 | 5 | Low Freq. |
| 12 | 5 | 10 | 15 | 20 | 25 | 0 | Low Freq. |

Appendix B

Clinical Results

Clinical results indicative of the efficacy of the present invention are provided hereinafter. In particular, representative results will be provided for the diagnostic effectiveness of the delayed binaural fusion test (DBFT) and for the efficacy of binaural phase-time delay (BPTD) compensating devices as clinically demonstrated by subjects having BPTD impairments, wherein the compensating device substantially alleviated the debilitating effects of such BPTD generated impairments.

Delayed Binaural Fusion Tests (DBFT)

The results of the preliminary studies presented below demonstrate the understanding of the significance and feasibility of the patent. In brief, the inventor's research documents that subjects with normal CANS function demonstrate optimal BPTDs at 0 msec. In other words, their auditory systems function optimally when acoustic stimuli have a matched-timed onset to the two ears. In contrast, these preliminary studies clearly demonstrated that subjects with CANS dysfunction show that matched-timed onset of acoustic signals (i.e., a 0 BPTD) do not result in optimal auditory function. In fact, optimal auditory function can only be obtained when a BPTD is induced between the two ears. The degree of the BPTD is quantified by DBFT results that are specific to each individual. The following descriptions of these preliminary studies will clarify what is meant by a BPTD and how a BPTD is induced.

The first study assessed the effects of BPTDs on auditory performance for individuals with both normal and atypical CANS function using the DBFT in a high-pass and low-pass frequency filtered format (404). This investigation concentrated on ascertaining the percentage change in auditory discrimination ability of bisyllabic words presented in a binaural interaction format at various msec lag times. A total of 115 subjects from 12 to 58 years of age were included in this study. Forty subjects were included in the normal CANS function group and 75 in the atypical CANS function group. The mean age for the normal CANS group was 25.74 with a range of 12 to 56. The mean age for the atypical CANS group was 20.3 years with an age range of 12 to 58 years. Selection for each group was determined by the results obtained on the central auditory processing (CAP) test battery. This battery included the Competing Sentences, Filtered Speech, and Binaural Fusion Tests of the Willeford Central Auditory Test battery (Willeford, 1977), the Ipsilateral/Contralateral Competing Sentence Test (IC/CST) (Willeford 1985a, 1985b, Willeford et al., 1985; Willeford et al., 1994), Synthetic Sentence Identification-Ipsilateral Competing Messages (SSI-ICM) (Jerger et al., 1974, 1975; Speaks et al., 1965), Dichotic Digits (Musiek, 1983; Musiek et al., 1979; Musiek et al., 1979) and Masking Level Differences (MLD) (Noffsinger et al., 1972; Olsen et al., 1976). Using one-way ANOVAs, test performance showed significant differences between the two groups as defined by performance on this test battery. A former study by Burleigh (1996) clearly showed significant differences between normal CANS function and atypical CANS function groups when using this test battery and agreed with these findings The low-pass and high-pass frequency filtered format, one version of the DBFT (404), and shown in Table 1, was used to quantify inherent BPTDs between ears. Statistically significant differences in speech recognition performance between normals and atypicals in the DBFT study of 115 subjects were observed. Significant differences in percent performance were also evidenced in all conditions for both ears except for a left ear lag at a 15 msec delay. The reason for this decrease in function for both normal and atypical groups at a 15 msec lag deserves further study. One can speculate that interaural timing for the left ear may reflect transfer of information at the level of the corpus callosum.

Further analysis showed that 78.67% of the atypical group showed a 20% or better increase in speech discrimination ability in noise with induced or compensating BPTDs as compared to the Omsec-lag condition. For those with normal CANS function, only 35% showed 20% or better improvement with the implementation of various lag times as compared to Omsec lag. FIG. 11 shows the percent of individuals who improved 20% or better for speech discrimination ability for both groups as compared to each subject's 0 msec score.

Figure 12:
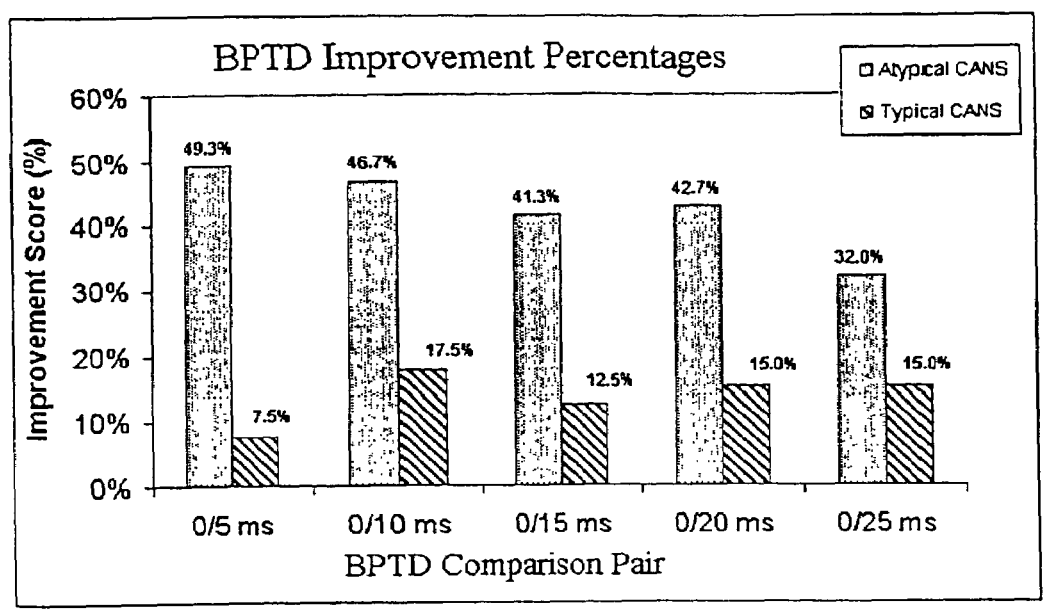

Statistically significant differences in auditory discrimination performance between normals and atypicals at 5 msec lag intervals are shown in FIG. 12. As demonstrated in this figure, significant differences in subjects who improved at least 20% from 0 msec were observed between groups for auditory conditions of 5 msec through 25 msec lags as compared to a baseline of 0 msec (absence of a time lag).

Standard Passive Earplugs

Initial clinical exploration of BPTDs involved the use of commercially available noise reduction filters that were originally designed for occupational safety. The specific earplug that has been used for this study is designed to attenuate damaging sounds while maintaining the amplitude of conversational frequencies in order to perform routine tasks while wearing the earplug. It is primarily used for industrial purposes. The earplug that was used for this portion of the clinical study is made of polyvinylchloride in a half shell earmold. This standard filtered earplug was modified to get the following clinical data. Due to the non-specific design of this earplug, only a single time delay was possible that was altered slightly by modifications to the length of the ear mold portion of the plug. The current art regarding diagnostics, as described earlier in this document, requires more flexibility with design and materials to accomplish closer control of and variations of the BPTDs. In particular it is evident that greater control of BPTDs at targeted frequencies is needed based on the diagnostic results. In particular, to utilize the commercially available earplug, we had to shorten the canal length in order to reduce the attenuation of the earplug while still providing a significant time delay from the filter elements. By shortening the length of the ear canal we could use the hard surface of the external auditory meatus itself for frequency filtering. Optimally, to achieve better performance with frequency filtering, a harder material should be used in the canal portion of the earplug. Further, to accommodate variations in phase differences between individuals with CANS dysfunction, different frequencies will be altered using acoustic filter elements within the canal and by altering the acoustic impedance of the materials surrounding the filter elements.

Commercially available filters are designed for wearing binaurally to reduce damaging noise while maintaining speech. It is not an intentional effect of the filter to produce a time delay in the acoustic signal. However, the inventors recognized that monaural use of such a filter was a passive filter approach to inducing a BPTD. The modifications to the filter to change the length of the filter were done on custom trial-and-error basis. The filter, with the resultant notched frequency configuration at 2000–3000 Hz, when worn monaurally, has the effect of a BPTD. The proposed passive device would be designed specifically for inducing a BPTD, and could be designed to induce the a predetermined BPTD obtained from the testing procedure described above. In addition, the BPTD could be limited to a particular frequency range (depending on PAT results) for specific amplitudes within the limitations of the capabilities of passive filtering elements. This would provide the ability to control the induced BPTD for individual fitting based on the diagnostic results. However, as mentioned earlier, the current art does not offer flexibility with size of BPTDs at specific frequencies for optimal auditory and human performance enhancement.

In order to understand the time delay in a plug, it is necessary to use a model that includes the complex response characteristics of the ducts. This is similar to the familiar insertion loss calculations that are performed in normal design; however, instead of only considering the magnitude of the response; the phase angle is also included. The model design however can include significant simplifications due to the long wavelength of the sound relative to the diameter of the ear plug duct.

Note that unilateral muffing does not result in a BPTD due to the gradual attenuation across all frequencies (i.e., no selective notch). With the muffs, from 250 Hz to 6000 Hz there is a 5–10 dB attenuation per octave.

Speech recognition scores were obtained in the sound field with the subject seated 3 feet from a front facing speaker. Monosyllabic words were presented at 40 dB SL re: sound field speech reception threshold in the presence of broad band noise (s/n=+5) presented from a back speaker.

Figure 13:
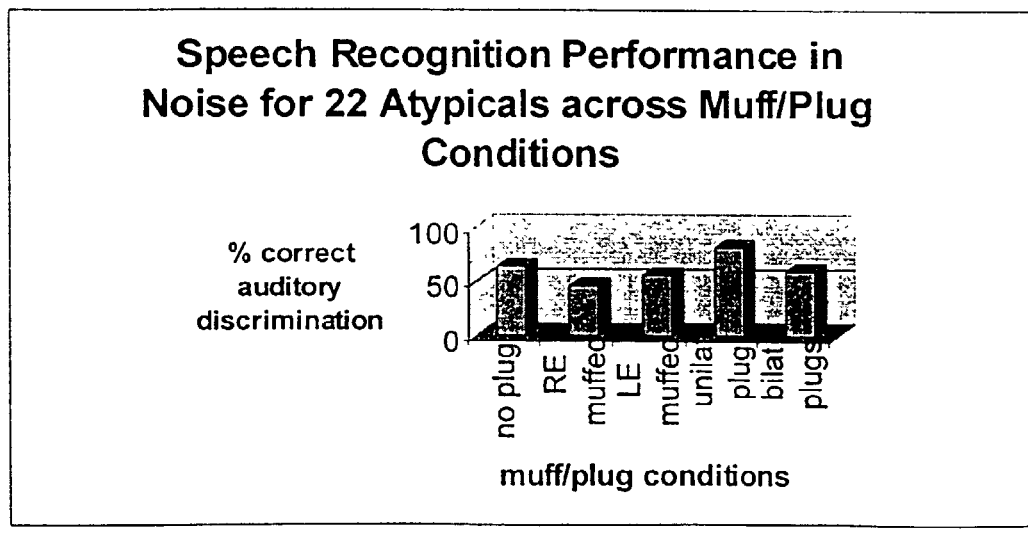

FIG. 13 shows speech recognition performance in noise for 22 individuals with CANS dysfunction. Five different conditions are shown in the figure.
1. "no plug": nothing in either ear
2. "RE muffed": hearing protection muff (noise reduction rating 25 dB—ANSI S12.6) worn over right ear
3. "LE muffed": hearing protection muff (noise reduction rating 25 dB—ANSI S12.6) worn over left ear
4. "unilat plug": standard filtered earplug worn in one ear only.
5. "bilat plug": standard filtered earplugs worn in both ears.

Of these five conditions, only condition 4 introduces a BPTD. Conditions 2 and 3 result in unilateral noise reduction and condition 5 results in bilateral high frequency noise reduction. All differences are statistically significant (p<0.05), except for the three conditions, which included the left ear muffed, and no plugs, bilateral plugging and no plugging, and left ear muffed and bilateral plugging. Of particular interest is the significant improvement in speech recognition with an induced BPTD ("unilat plug"), P<0.0001. Noise reduction without a BPTD (unilateral muff or bilateral earplugs) does not result in enhanced speech recognition.

FIG. 14 shows speech recognition ability in noise results for 12 individuals without CANS dysfunction. Five different conditions are shown in the figure.
1. "no plug": nothing in either ear
2. "RE muffed": hearing protection muff (noise reduction rating 25 dB—ANSI S12.6) worn over right ear
3. "LE muffed": hearing protection muff (noise reduction rating 25 dB—ANSI S12.6) worn over left ear
4. "RE plug": standard earplug worn in right ear only.
5. "LE plug": standard earplug worn in left ear only.

The "no plug" results are significantly (p<0.01) greater than any of the other conditions. These results demonstrate the importance of synchronous binaural processing of auditory input for enhanced speech discrimination in noise for individuals with a normal CANS. Furthermore, these results indicate that unilateral noise reduction (conditions 2 and 3) or introducing a BPTD (conditions 4 and 5) do not enhance speech discrimination in noise for individuals with normal CANS function.

Note that speech discrimination results for the atypical group under condition 1 ("no plug") are significantly lower than those for the normal group under condition 1 ("no plug"). Note also that under condition 4 ("unilat plug"), the atypical group performs at approximately the same level as the normal group does under condition 1 ("no plug").

Preliminary Data of BPTDs on Human Performance Using Electronic Device

Ten normal CANS subjects and 10 atypical CANS subjects were selected for various human performance testing using the prototype BPTD electronic device. The mean age of the 10 normal subjects was 31 years with an age range of 21–43 years. In this group, five individuals were male and five were female. In the atypical CANS group, the mean age was 29.1 years with an age range of 15 to 47 years. Seven females and 3 males were included in this group. All subjects in the two groups passed the initial subject selection criteria. The ten subjects that were included in the atypical CANS group failed at least one test in either ear in the CAP test battery. Further, to provide for a balancing of BPTDs for the normal group, subjects for the atypical group were selected when they showed maximum improvement for the DBFT with a 2.5–7.5 msec BPTD to either the right or left ear.

Another version of the DBFT (406) was developed to include time-lagged bisyllabic stimuli that were presented in 2.5 msec increments (the previous DBFT used 5 msec increments). This version included thirty bisyllabic words per list (4 lists) that were lagged in time between ears of 0 msec, 2.5 msec, 5 msec, and 7.5 msec and recorded in a CD format with an 8-talker babble (s/n ratio of +2 dB) embedded in the background and presented binaurally. These words were presented under earphones at 40 dB sensation level relative to pure tone averages for both ears. The lag ear was determined by results from the DBFT 5 msec version (404).

The highest speech recognition percent score for bisyllabic words was determined to be the "optimal" msec setting for the BPTD device for atypical CANS subjects. The optimal condition for normal CANS subjects was randomized at 2.5 msec, 5 msec, and 7.5 msec. Statistical analysis showed that these word lists were equivalent.

The 5 auditory conditions used in the preliminary studies were as follows: (1) natural condition which was unoccluded with 8-talker babble presented at 40 dB HL, (2) quiet which consisted of an unoccluded condition with 8-talker babble presented at 25 dB HL, (3) optimal condition using the BPTD electronic device in the presence of 40 dB HL 8-talker babble; (4) 0 msec condition using the BPTD electronic device with 40 dB HL 8-talker babble, and (5) opposite BPTD (same setting but in opposite ear) from the optimal setting (e.g., if "optimal" was a 5 msec lag to the right ear, then "opposite" is a 5 msec lag to the left ear). Not all tests examined condition 5.

Auditory Discrimination

Percent improvement in speech recognition ability using the BPTD device was assessed using four thirty-bisyllabic word lists that were recorded on a CD at 0 msec (408). Auditory stimuli were presented in the sound field from a front facing speaker two meters from the individual. Test stimuli were presented at 45 dB sensation level (re: sound field speech reception threshold) in the presence of an 8-talker babble recorded at a +2 s/n ratio. Both stimuli were presented from the front speaker in a double-walled sound proof room.

Figure 15:
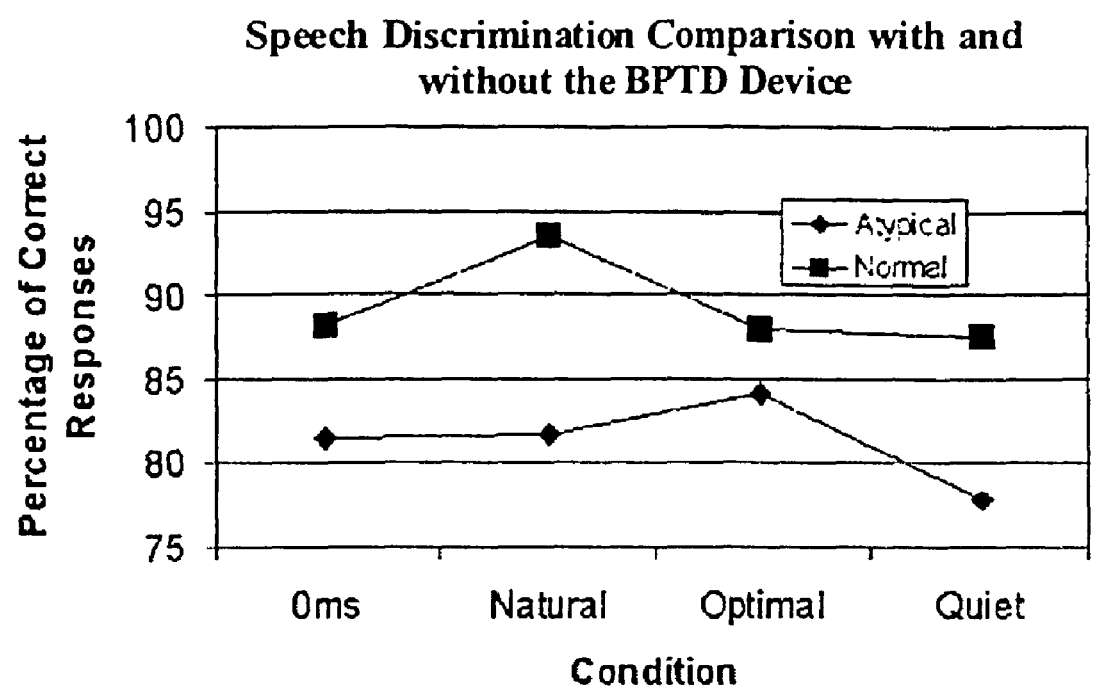

Results (see FIG. 15) under these conditions showed a type effect across conditions (p=0.0039). There was also a condition effect (p=0.0474). The atypical group showed the greatest percent improvement for speech recognition ability with the BPTD device set at their "optimal" lag time.

Motor

Gait studies were performed in a controlled uniform sound environment—a semi-anechoic chamber. Reverberation times were long enough (or amplitudes sufficiently low) that the room was taken as representative of the sound field in an open or large room with high damping. The ambient sound level in the chamber was 45 dB SPL (Metrosonics dosimeter, Model dB307, Class Type 2A, Rochester, N.Y.). Sound sources were then introduced into the chamber under controlled amplitude and directionality. This is a highly controlled sound field relative to all previous gait studies in the literature.

Speakers were placed in the anechoic chamber at 0 ((far left), 45 (, 90 ((center), 135 (, and 180 ((far right) locations in a clockwise direction relative to the direction of travel. The five sound sources were randomly presented to create the general localized sound condition (LS). Two additional cases were run in the chamber without speaker input: walking with and without earmuffs (Peltor, Model H6A/V) created the general reduced sound level condition (RS). For the BPTD device study, the center speaker was used.

The speaker output (i.e., sound source) was a tape-recorded eight-person multi-talker babble presented at a sound level that was within three dB of a 56 dB SPL in the chamber calibrated gait area. To reduce the influence of visual stimuli, all materials used in the chamber were monochromatic (i.e., either gray or black) and the room lighting was reduced to approximately 0.9 footcandles (equivalent to a moderately lighted parking lot).

A calibrated three-dimensional video gait analysis (Peak Motus™, Englewood, Colo.) was completed with three camera views. The three cameras recorded each subject walking straight ahead within the calibrated area at a comfortable pace for two strides. The subject repeated each condition until three to five gait cycles were recorded between consecutive heel strikes of the same foot. As part of the motion analysis system, retro-reflective markers were mounted on the skin using 3M™ hypoallergenic double-sided tape. On the head, two markers were placed on a spandex swim cap pointing upward directly above the ears. Body markers were placed on the vertebra prominens (C7 vertebra), shoulders, elbows, wrists, greater trochanters, knees, and ankles.

To normalize the gait data for subject stature, the kinematic data were divided by the subject's height in meters. The following gait parameters will be presented: walking speed (% height/sec), stride width (% height), and center of mass position (COM) (% height). The relative COM (COM Del) was the difference of the lateral COM position from the origin between the first heel strike and the time of measurement. The Root Mean Square Error (RMSE) method was used to calculate the mean lateral deviation from a straight-line path of the COM.

A study was performed assessing gait while using the electronic device set at an optimal BPTD (Burleigh et al., 1999). Optimal BPTD was determined by the DBFT results, (i.e., if a subject had the highest DBFT score with a 5 msec delay to the right ear, a right 5 msec delay was the "optimal" setting). The BPTD device was used with 6 normal and 6 atypical subjects in three different conditions: "optimal," "0 msec," and "opposite" as described above.

Figure 16:
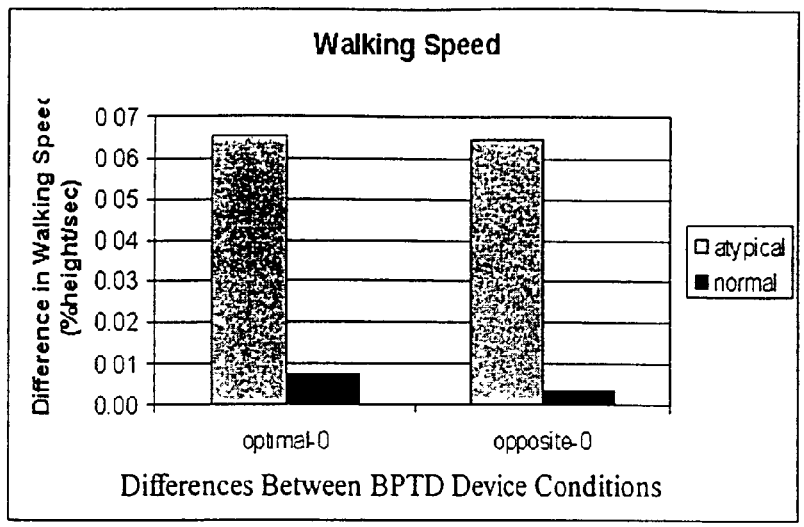
Figure 17:
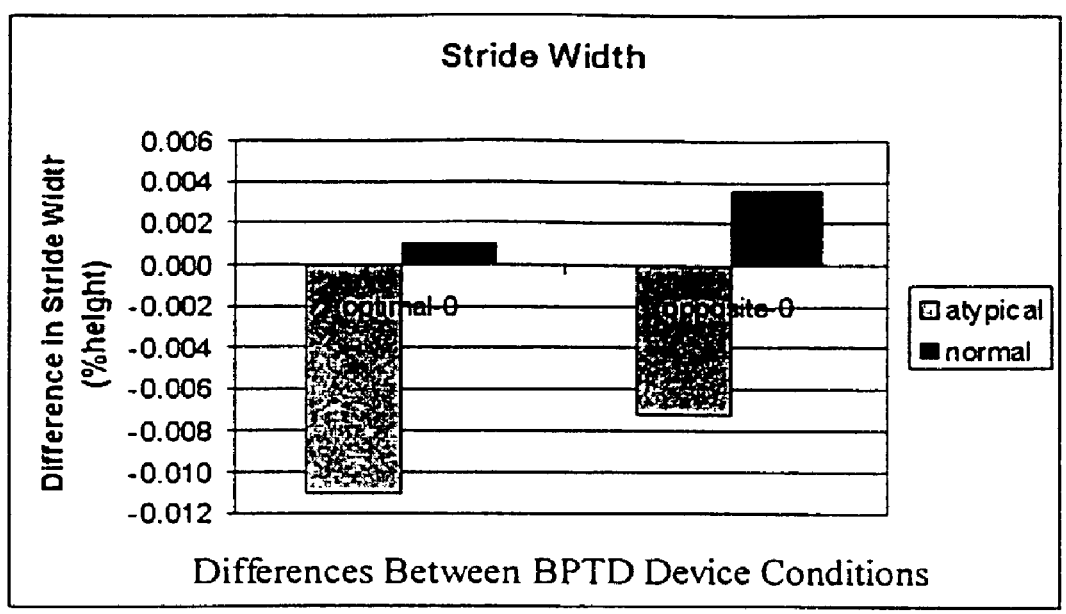

FIGS. 16, 17, and 18 show the walking speed, stride width and RMSE results for the atypical and normal groups under the different BPTD device conditions. The data graphically presents the differences in these parameters between the three BPTD device conditions. For example, the first bar in FIG. 16 shows the average of the differences in walking speed for each of the atypical subjects between the "optimal" and "0 msec" conditions.

It is evident that atypical group's gait is significantly improved (i.e., they walk faster) under both the "optimal" and "opposite" BPTDs, compared to the absence of a BPTD (0 msec), while the BPTD settings have little effect on the normal subjects' gait. The differences between the atypical and normal groups in the walking speed figure are not quite statistically significant (p=0.074 for "optimal-0" and p=0.064 for "opposite-0"). Given the relatively small number of subjects in this study, and large variation in gait parameters, this was not surprising. However, the trends are quite strong and with a larger number of well-matched (on gender and age) subjects, significant differences are expected.

The results for stride width (FIG. 17) and Root Mean Square Error (RMSE) (FIG. 18) are similar, showing an improvement in gait (decrease in stride width and RMSE) for the atypicals under both the "optimal" and "opposite" conditions, and little effect on the gait of the normals. The differences between the atypicals and normals for stride width were not statistically significant for the "optimal-0" case (p=0.1042), but were for the "opposite-0" case (p=0.0422). For RMSE (FIG. 18) the differences between the atypicals and normals were not significant (p=0.1552 and p=0.1012, respectively for "optimal-0" and "opposite-0").

The decrease in stride width and RMSE is seen as an improvement in gait as the decreases tended to bring the values of these parameters for the atypicals closer to the values for the normals. While the gait of the normal subjects was impacted very little by the device, as compared to the atypical group, the graphs indicate a trend that the "optimal" and "opposite" BPTDs actually degrade the normal subjects' gait. This trend supports the notion that while an induced BPTD in a normal CANS system is disruptive, it can be accommodated.

It was surprising that the "optimal" and "opposite" settings both seem to enhance gait in the atypical group. Perhaps this is evidence that while BPTDs impact gait, the effect is different from the impact of BPTDs on other aspects of human performance, such as speech discrimination.

Interestingly, most changes in individual atypical subjects' gait under the different BPTD device conditions were significant. For example, most atypical subjects walked significantly faster under the BPTD device "optimal" setting when compared to their walking speed under the "0 msec" setting, using multiple trials under each condition as the multiple measures.

Speech

Acoustic measures of diadochokinetic rate or maximum repetition rate for non-speech material includes: duration in msec of 5 correct syllable sequences out of 7 consecutive utterances. This measure was used as an assessment of articulatory speed; however, because only correct syllable productions were counted, it probably more accurately reflected articulatory efficiency. Syllable and pause durations were also measured as were irregularities or variances among successive syllable and pause durations within each condition.

Results of performance of these tasks under auditory conditions in normal and atypical subjects revealed statistically significant differences in articulatory efficiency, syllable duration and variances in syllable and pause duration when comparing those persons with normal and atypical CANS function (p<0.05 for each). This suggested that while all subjects were considered normal speakers, differences in abilities to make rapid alternating movements differ in persons with atypical versus normal CANS function.

There was also a statistically significant difference in articulatory efficiency and intersyllabic pause durations among experimental auditory conditions for both groups (p<0.05). Durations for completions of 5 accurate syllable sequences and intersyllabic pauses were shorter under the optimal or accommodating auditory condition compared to conditions of 0 msec delay or reduced noise. These findings suggest that not only do auditory conditions impact the performance of rapidly alternating nonspeech movements, but that specific adjustments in binaural timing between ears may improve performance over conditions where no differences are introduced.

In oral reading of an 85-word paragraph, perceptual measures were taken of the number of dysfluencies and reading speed in words per second. Perceptual dysfluency types included: part and whole word repetitions, phrase repetitions/restarts, prolongations, phonatory disruptions, interjections, blocks, and pauses. This system of dysfluency classification was modified from Kent, 1994.

A review of number of dysfluencies in oral reading provided the most convincing evidence of benefits of accommodating BPTDs. While there were statistically significant differences in the total number of dysfluencies between normal and atypical experimental groups (p<0.05), for this parameter there was also a statistically significant condition-type interaction (p<0.05) suggesting that the differences in performance in favor of the normal subjects was a function of the auditory condition. Specifically, as can be seen in FIG. 19, not only do the persons without CANS dysfunction show a flatter profile of performance across auditory conditions when compared with those with CANS deficits, those with atypical CANS function make the fewest errors, performing very close to normal at their optimal or accommodated auditory condition. In fact, statistically significant differences are apparent between normals and atypicals under natural and 0 msec conditions but are not at the accommodating condition. Further, the performance of atypicals in pairwise condition comparisons, reveals statistically fewer dysfluency errors made under optimal or accommodating auditory condition when compared against each: 0 msec, natural and reduced noise conditions.

Reading speed as measured by words per second in an 85-word oral reading sample revealed statistically significant differences when comparing those persons with normal and atypical CANS function (p<0.05). It should also be noted that although statistically significant differences were not observed in pairwise comparisons across auditory conditions for the subjects with atypical CANS function, the fastest reading rate condition for this group was their optimal or accommodated condition.

THE COMMERCIALLY AVAILABLE STANDARD PASSIVE EARPLUGS USED IN THIS STUDY IS NOT AN EMBODIMENT OF THE INVENTION (see paragraph below) BUT ILLUSTRATES VARIOUS FEATURES OF THE METHOD UTILIZED AND DESCRIBED HEREIN.

The foregoing discussion of the invention has been presented for purposes of illustration and description. Further, the description is not intended to limit the invention to the form disclosed herein. Consequently, variation and modification commensurate with the above teachings, within the skill and knowledge of the relevant art, are within the scope of the present invention. The embodiment described hereinabove is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. An apparatus for developing a binaural phase time delay profile (BPTD) of an individual, comprising:
   means for separating spoken words into high frequency and low frequency bands;
   means for delaying one of the bands relative to the other band;
   means for presenting the delayed band to one ear and the undelayed band to the other ear;
   means for measuring the individual's comprehension of the words at a variety of delays;
   means for determining the overall phase delay at which comprehension is optimal;
   means for providing a pure tone;
   means for dividing the pure tone into two channels;
   means for applying a phase shift to one of the channels;
   means for presenting the phase shifted channel to one ear, and the non-phase shifted channel to the other ear;
   means for varying the amplitude and the frequency of the tone;
   means for finding a threshold (lowest amplitude at which the tone is heard) for various frequency tones at various phase shifts; and means for assigning an optimal phase shift at the various frequency tones according to the lowest amplitude at which each tone is heard.

2. The apparatus of claim 1, wherein the means for determining an overall relative delay and the means for determining a phase shift profile are implemented as an electronic device (500) including:
   means (512) for varying overall relative delay;
   means (514) for varying phase shift profile; and
   means for assessing the individual (520) at various overall relative delays and phase shift profiles to determine an optimal overall relative delay and an optimal phase shift profile.

3. The apparatus of claim 1, further including means for determining an amplitude modification profile for the individual.

4. A method for developing a binaural phase time delay profile (BPTD) of an individual comprising the steps of:
   separating spoken words into high frequency and low frequency bands;
   delaying one of the bands relative to the other band;
   presenting the delayed band to one ear and the undelayed band to the other ear;
   measuring the individual's comprehension of the words at a variety of delays;
   determining the overall phase delay at which comprehension is optimal;
   providing a pure tone;
   dividing the pure tone into two channels;
   applying a phase shift to one of the channels;
   presenting the phase shifted channel to one ear, and the non-phase shifted channel to the other ear;
   varying the amplitude and the frequency of the tone;
   finding a threshold (lowest amplitude at which the tone is heard) for various frequency tones at various phase shifts; and
   assigning an optimal phase shift at the various frequency tones according to the lowest amplitude at which each tone is heard.

5. The method of claim 4, further including the step of performing conventional hearing tests on the individual.

6. An apparatus to develop a binaural phase time delay profile of an individual comprising:
   a high frequency and low frequency bands separation element;
   a frequency band delay element;
   a presentation element adapted to present a delayed band to one ear and an undelayed band to another ear;
   a comprehension measurement element responsive to a variety of delays;
   an optimal overall phase delay determination element;
   a pure tone element;
   a two channel divider responsive to said pure tone element;
   a phase shift element responsive to one of the channels of said two channel divider;
   a presentation element adapted to present a phase shifted channel to one ear;
   a non-phase shifted channel to another ear;
   a tone amplitude and frequency variation element;
   a threshold determination element responsive to said tone amplitude and frequency variation element; and
   an optimal phase shift assignment element responsive to the lowest amplitude at which each tone is heard.

7. The apparatus of claim 6, wherein the overall relative delay determination element and the phase shift profile determination element are implemented as an electronic device comprising:
   an overall relative delay variation element;
   a phase shift profile variation element; and
   an individual assessment element responsive to said overall relative delay determination element and said phase shift profile variation element.

8. The apparatus of claim 6, further comprising an amplitude modification profile determination element.

* * * * *